United States Patent [19]

Packard et al.

[11] Patent Number: 5,364,619
[45] Date of Patent: Nov. 15, 1994

[54] ONCOIMMUNINS

[75] Inventors: Beverly Packard; Akira Komoriya, both of Rockville, Md.

[73] Assignee: The United States of America as represented by the Secretary of the Department of Health and Human Services, Washington, D.C.

[21] Appl. No.: 764,695

[22] Filed: Sep. 23, 1991

Related U.S. Application Data

[63] Continuation-in-part of Ser. No. 707,136, May 31, 1991.

[51] Int. Cl.$^5$ .............................................. A61K 37/02
[52] U.S. Cl. .................................. 424/85.1; 424/85.2; 530/350; 530/351; 514/2
[58] Field of Search ............................ 424/85.1, 85.2; 530/350, 351; 514/2

[56] References Cited

U.S. PATENT DOCUMENTS 4,863,727 9/1989 Zimmerman et al. .............. 424/85.2

OTHER PUBLICATIONS

R. Andreesen & B. Hennemann "Adoptive Immunotherapy with Autol. Macrophage . . . Perspectives", Macrophage, Ann Conf upper Rhine Univ(II) Pathobiology 1991; 59; 259–63.

Bartholeyns, J. M. Lopez and R. Andreeson "Adoptive Immunotherapy Clinical Results,"Anticancer Res. 11: 1201–1204 (1991).

Andreesen et al. "A New Approach to . . . Blood Monocytes" Cancer Prevention and Detection, vol. 15, Issue #5, pp. 413–421.

Packard, B. S. "Mitogenic stimulation of human tumor-infiltrating Lymphocytes . . . cell lines", PNAS, 87: pp. 4058–4062, 1990.

Vose, B. M. et al. Human Tumour Antigens Defined by Cytotoxicity and Proliferative Responses of Cultured Lymphoid Cells, Nature (London), vol. 296, pp. 359–361 (1982).

Vose, B. M. et al., Specific Cytotoxicity Against Autologous Tumours and Proliferative Responses of Human Lymphocytes Grown in Interleukin 2, Int. J. Cancer, vol. 29, pp. 33–39 (1982).

Vanky, F. et al., Lysis of Tumor Biopsy Cells by Autologous T Lymphocytes Activated in Mixed Cultures and Propogated with T Cell Growth Factor, J. Exp. Med. vol. 155, pp. 83–95 (1982).

Mitsuya et al., Generation of an HLA-Restricted Cytotoxic T Cell Line Reactive Against Cultured Tumor Cells from A Patient Infected with Human T Cell Leukemia/Lymphoma Virus, J. Exp. Med., vol. 158, pp. 994–999 (1983).

De Vries, J. E. et al., Cloned Human Cytotoxic T Lymphocyte (CTL) Lines Reactive With Autologous Melanoma Cells, J. Immunol., vol. 132, pp. 510–519 (1984).

Slovin, S. F. et al., Cellular Immune Response to Human Sarcomas: Cytotoxic T Cell Clones Reactive With Autologous Sarcomas, vol. 137, pp. 3042–3048 (1986).

Itoh, K. et al., Interleukin 2 Activation of Cytotoxic T-Lymphocytes Infiltrating into Human Metastatic Melanomas, Cancer Res., vol. 46, pp. 3011–3017 (1986).

Rosenberg et al., A New Approach to the Adoptive Immunotherapy of Cancer with Tumor-Infiltrating Lymphocytes, Science, vol. 233, pp. 1318–1321 (1986).

Rabinowich, H. et al., Functional Analysis of Mononuclear Cells Infiltrating into Tumors: Lysis of Autologous Human Tumor Cells by Cultured Infiltrating Lymphocytes, Cancer Res., vol. 47, pp. 173–177 (1987).

Miescher, T. et al., Clonal and Frequency Analyses of (List continued on next page.)

Primary Examiner—Howard E. Schain
Assistant Examiner—R. Lynn Touzeau
Attorney, Agent, or Firm—Townsend and Townsend Khourie and Crew

[57] ABSTRACT

The present invention relates, in general, to oncoimmunins. In particular, the present invention relates to oncoimmunin-lymphoid factor and oncoimmunin-myeloid factor, pharmaceutical compositions of said factors, and methods of use of said factors.

15 Claims, 17 Drawing Sheets

OTHER PUBLICATIONS

Tumor–Infiltrating T Lymphocytes From Human Solid Tumors, J. Immunol., vol. 138, pp. 4004–4011 (1987).

Kadin, R. L. et al., Tumor-derived Interleukin-2-dependent Lymphocytes in Adoptive Immunotherapy of Lung Cancer, vol. 24, pp. 76–86 (1987).

Rosenberg, S. A. et al., Use of Tumor-Infiltrating Lymphocytes and Interleukin-2 in the Immunotherapy of Patients With Metastatic Melanoma, N. Engl. J. Med., vol. 319, pp. 1676–1680 (1988).

Smith, K. A. Interleukin-2: Inception, Impact, and Implications, Science, vol. 240, pp. 1169–1176 (1988).

Topalian, S. L. et al., Expansion of Human Tumor Infiltrating Lymphocytes for Use in Immunotherapy Trials, J. Immunol., vol. 102, pp. 127–141 (1987).

Packard, B. S., Identification of a Synthetic Nonapeptide Sequence that Inhibits Motility in Culture of a Melanoma Subclone that Possesses a High Metastatic Potential, Proc. Natl. Acad. Sci., vol. 84, pp. 9015–9019 (1987).

Kirnbauer, R. et al., IFN-$\beta 2$ Cell Differentiation Factor 2, or Hybridoma Growth Factor (IL-6) is Expressed And Released by Human Epidermal Cells and Epidermoid Carcinoma Cell Lines, J. Immuno., vol. 142, pp. 1922–1928 (1987).

Packard, B. S., The Use of Tumor-Infiltrating Lymphocytes in Cancer Therapy, In: Progress Regional Cancer Therapy, eds Jakcez, R. et al., (Springer Heidelberg), pp. 293–303 (1990).

Smith, K. A., The Interleukin 2 Reporter, Adv. Immunol., vol. 42, pp. 165–179 (1988).

Quinan, C. V., Points to Consider in the Collection, Processing and Testing of Ex Vivo Activated Mononuclear Leukocytes for Administration to Humans, Publication of Center for Biologics Evaluations and Research, Food and Drug Administration (1989).

Packard, Beverly S., Mitogenic stimulation of human tumor–infiltrating lymphocytes by secreted factor(s) from human tumor cell lines, Proc. Natl. Acad. Sci. USA (1990), vol. 87, pp. 4058–4062.

Packard, Beverly S. et al., Identification of a New Growth Factor for Lymphocytes: Mitogenic Stimulation of Lymphocytes by Tumor Cell Lines, Federation of American Society of Experimental Biology (Apr. 1991) Atlanta, Ga.

Packard, Beverly, Identification of a new class of growth factors: tumor-derived lymphocytes mitogens, Biophysical Society of America (Feb. 1991) San Francisco, California.

Packard, Beverly S., Mitogenic Stimulation of Human T Cells by Solid Tumor Lines Mediated by Secreted Proteins, Biophysical Society of America (Feb. 1990), Baltimore, Maryland.

Packard, B., Mitogenic stimulation of human tumor infiltrating lymphocytes by human cell lines, American Association of Cancer Research (May 1990), Washington, D.C.

Packard, Beverly S. et al., Mitogenic stimulation of human tumor infiltrating lymphocytes by human cell lines (Mar. 1990), Florence, Italy.

Packard, B. S., A New Mitogen Derived From a Tumor Cell Line for Tumor Infiltrating Lymphocytes (TILS), American Society of Cell Biology (Nov. 1989), Houston, Texas.

Packard, Beverly, A New Mitogen for Tumor Infiltrating Lymphocytes (TILS) Derived from a Tumor Cell Line (Nov. 1989), Hilton Head, South Carolina.

Packard, Beverly S., Mitogenic Stimulation of Human T Cells by Solid Tumor Lines Mediated by Secreted Proteins (Jul. 1989), Berlin, West Germany.

Treves, Abraham, et al., Immunotherapy of Lethal Metastases by Lymphocytes Sensitized Against Tumor Cells In Vitro., J. Natl. Cancer Inst., vol. 54, No. 3, pp. 777–780 (1975).

Lee, S. K. et al., Autologous Leukemia–Specific T-Cell-Mediated Lymphocytotoxicity in Patients with Acute Myelogenous Leukemia, J. Exp. Med., vol. 147, pp. 912–922 (1978).

Zarling, J. M. et al., Continuous Culture of T Cells Cytotoxic for Autologous Human Leukaemia Cells, Nature (London), vol. 280, pp. 685–587 (1979).

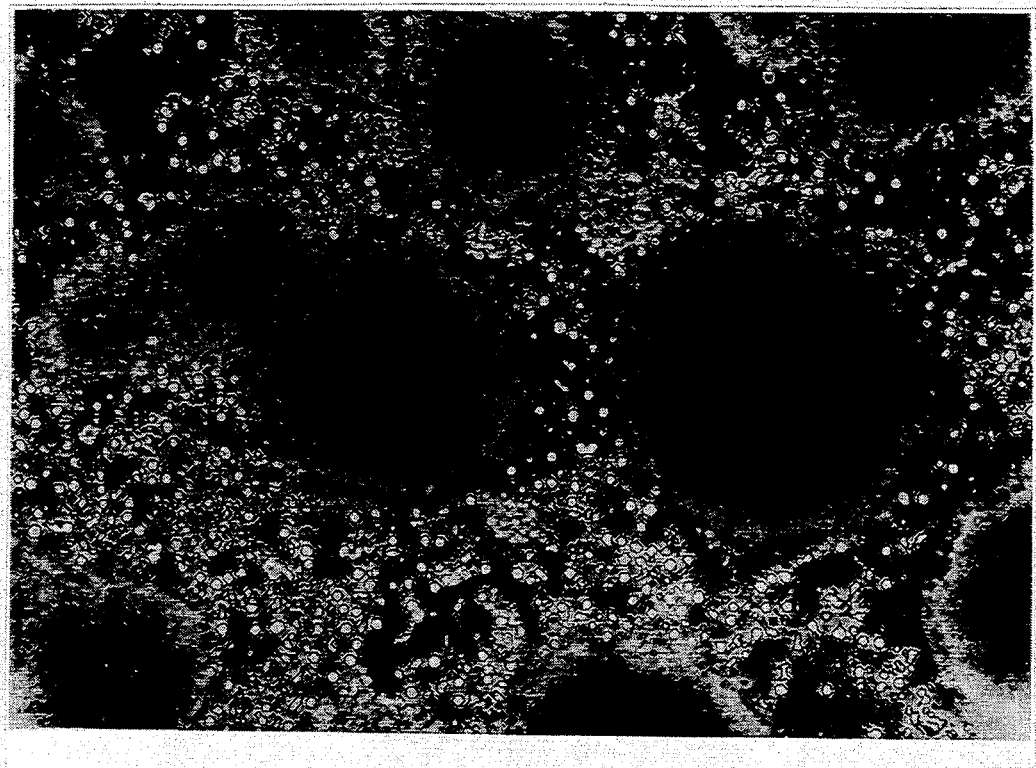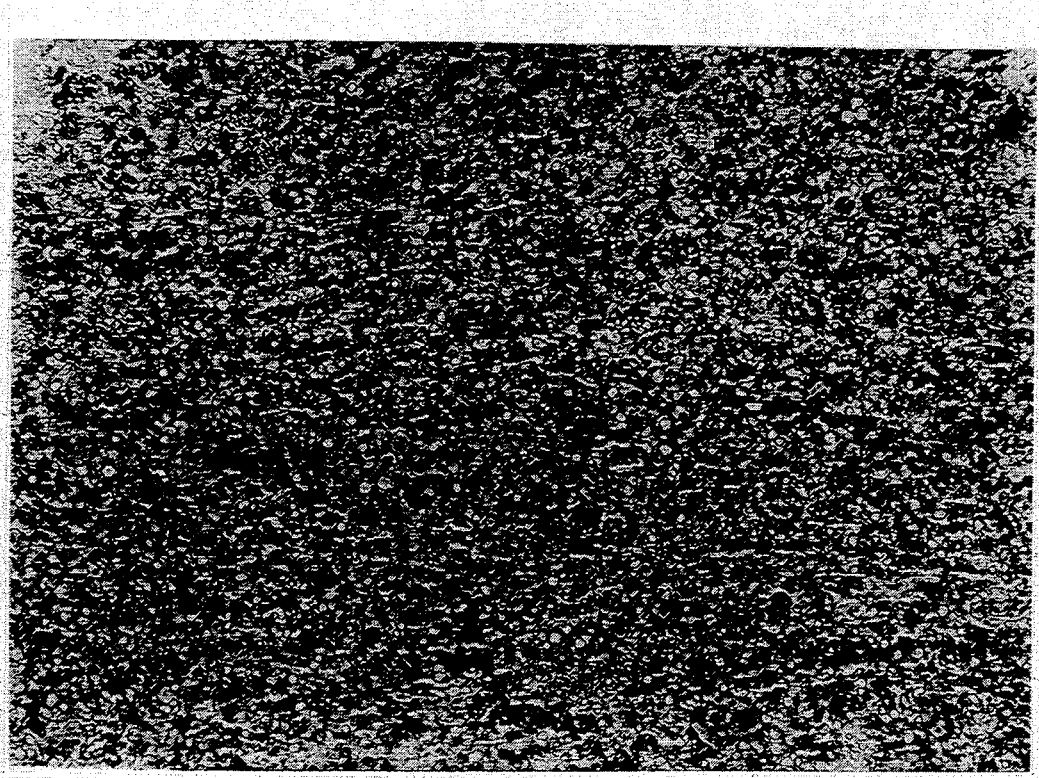
FIG. 1.

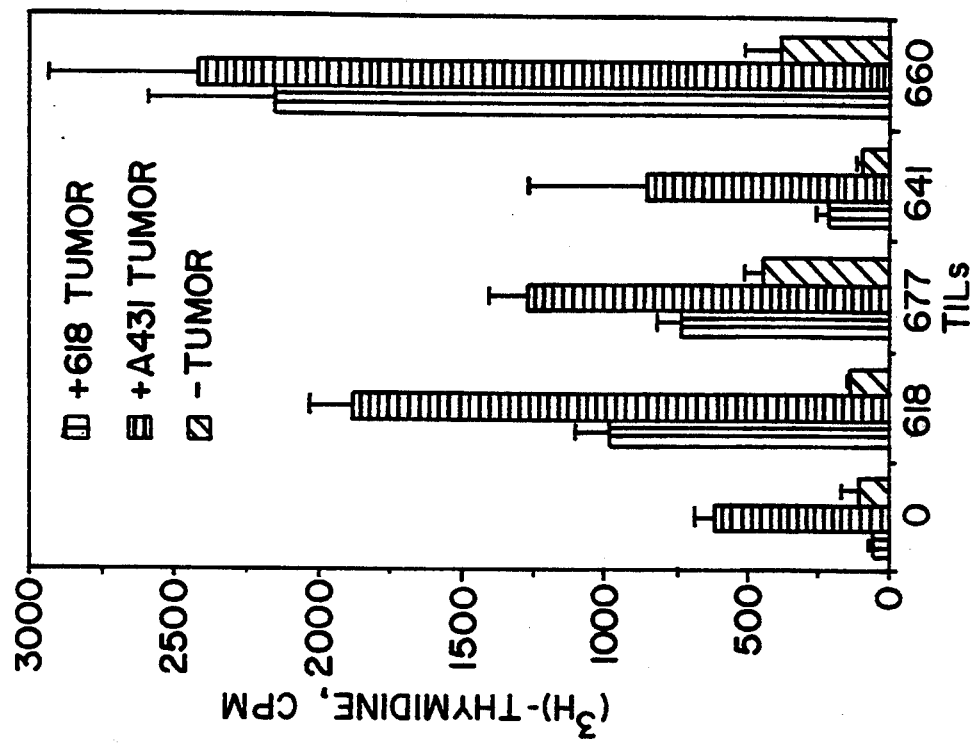
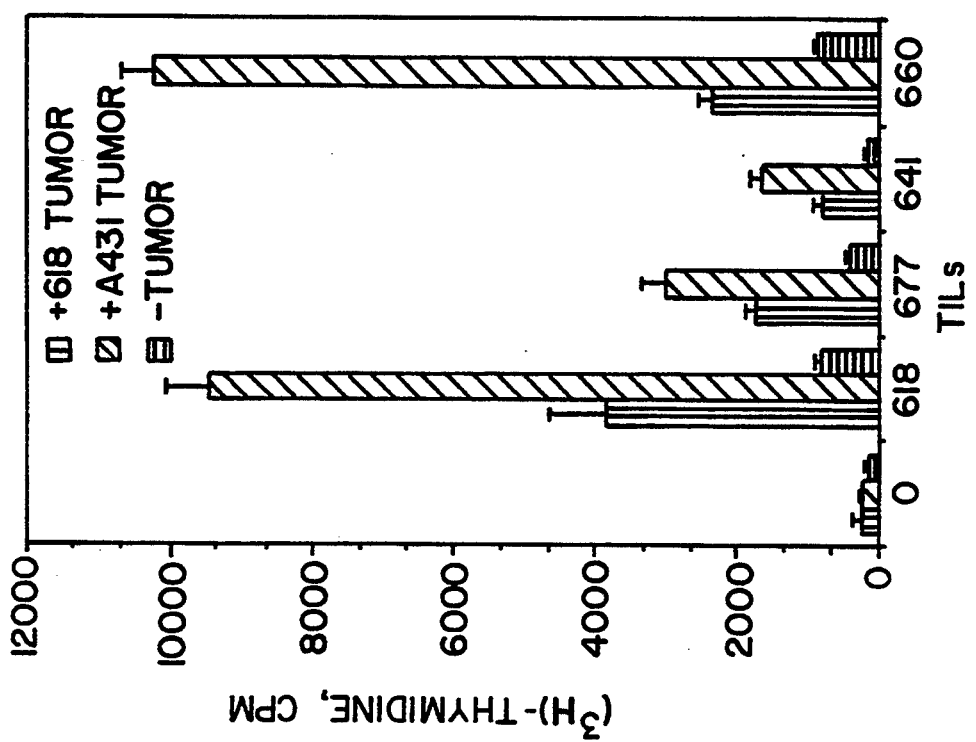

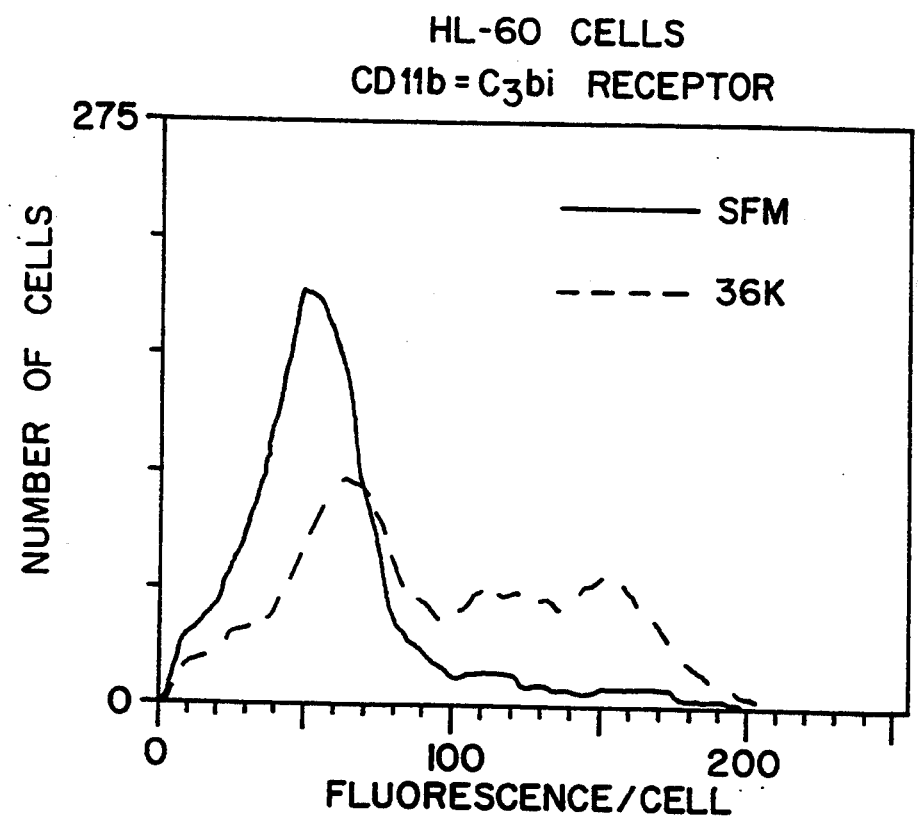
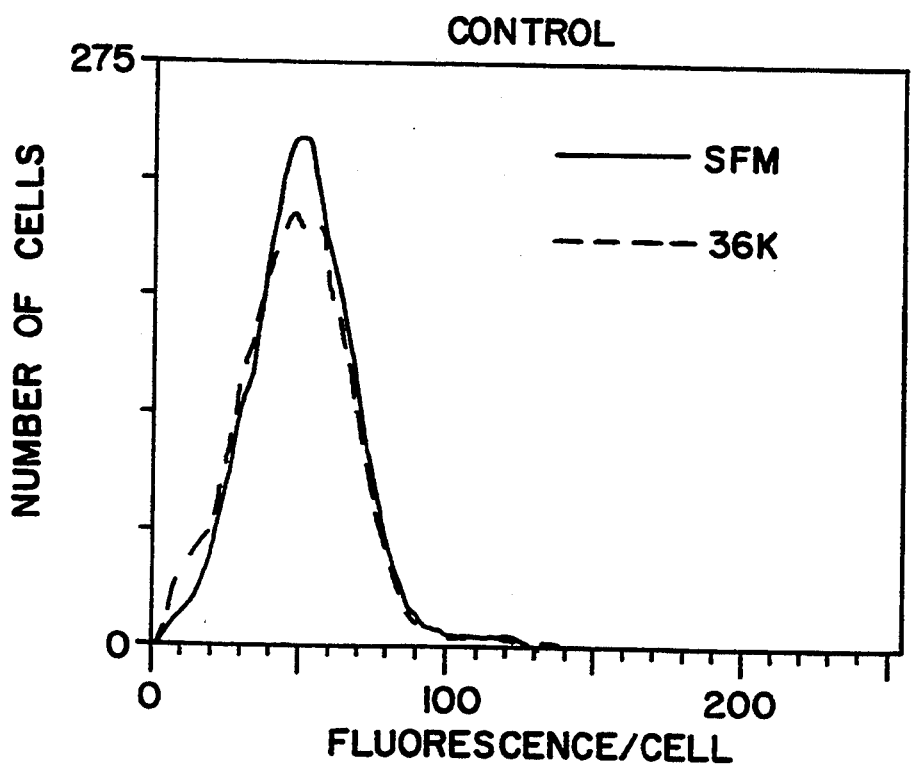
FIG. 14.

ONCOIMMUNINS

BACKGROUND OF THE INVENTION

This application is a continuation in part of U.S. application Ser. No. 07/707,136, filed May 31, 1991, pending, the content of which is incorporated herein by reference.

FIELD OF THE INVENTION

The present invention relates, in general, to oncoimmunins. In particular, the present invention relates to oncoimmunin-lymphoid factor and oncoimmunin-myeloid factor, pharmaceutical compositions of said factors, and methods of use of said factors.

BACKGROUND INFORMATION

The idea that the tumor environment is intrinsically immunogenic and, therefore, contains lymphocytes with the potential to induce tumor regression has led to the use of tumor-infiltrating lymphocytes (TILs) in clinical trials (1–14). In this procedure lymphocytes are grown ex vivo directly from tumors in the presence of the lymphokine interleukin 2 (IL-2); patients are reinfused with their TILs after the latter have been expanded in culture for several weeks. Although 60% of metastatic melanoma patients who had previously received any immunotherapy showed objective responses in the largest clinical TIL trial to date (15), the characteristics of the tumor environment that produces TIL's in vivo remain unclear.

Two classes of stimuli—one derived from cell-cell contact between tumor cells and immunocytes and the other from soluble factors—may influence T-cell homing and proliferation. IL-2 is a potent mitogen for T cells, the cell type of TILs used (Table 1); however, its biosynthesis appears to be confined to immunocytes (16). This facts is consistent with the current belief that immunologically competent cells such as lymphocytes and monocytes represent the major sources of secreted mitogenic stimulation for lymphocytes. In this study the subject of soluble factors secreted by tumor cell lines as sources of stimuli for lymphocyte proliferation was addressed.

As a starting point for this work, the issue of whether a tumor cell line established from a melanoma tumor could stimulate the growth of TILs derived from melanoma masses was examined. After confirming the amplification potential of three melanoma cell lines, a non-melanoma line was tested for the same bioactivity and found to be at least as potent a mitogenic source; tumor-derived mitogenic activity for TILs could be ascribed to secreted factor(s) as mitogenic activity for TILs was found in its serum-free supernatant. Immunologic and proliferative assays indicate nonidentity of at least one secreted factor with any previously characterized lymphokine.

SUMMARY OF THE INVENTION

It is a general object of this invention to provide a factor.

It is a specific object of this invention to provide an oncoimmunin-lymphoid factor having the ability to stimulate human T-lymphocyte mitogenesis.

It is a further object of the invention to provide a method of stimulating human T-lymphocyte mitogenesis.

It is another object of this invention to provide an oncoimmunin-myeloid factor having the ability to induce myeloid differentiation.

It is a further object of the invention to provide a method of inducing myeloid differentiation.

It is another object of the invention to provide pharmaceutical compositions comprising the factor above-described factors.

Further objects and advantages of the present invention will be clear from the description that follows.

BRIEF DESCRIPTION OF THE DRAWINGS

FIG. 1. TILs growing in the absence (a) and presence (b) of 618 tumor cells. Tumor cells were plated at $5 \times 10^4$ per 0.2 cm$^2$ in DMEM/10% FCS. After 1 day the medium was changed to SFM and left for at least 48 hr. TILs at $1 \times 10^6$ cells per ml were plated without and with a confluent monolayer of 618 tumor cells. Twenty-four hours later the cultures were examined and photographed. In the former, lymphocytes grow as large clusters, whereas in the latter cellular heterophilia—i.e. adhesion between lymphocytes and tumor cells—predominates over cellular homophilia—i.e., adhesion among lymphocytes. Although TILs 618, 660 and 667 could lyse autologous tumor cells that had been frozen but never cultured, they showed virtually no lyric capability against any of the cultured tumor lines in the configuration used in this study—i.e., as adherent monolayers. This sharply contrasts with lymphokine-activated killer cells, which effectively lysed all tumor lines used in this work ($\times 110$).

FIG. 3. Effect of serum on tumor-potentiated TIL proliferation. Comparison of enhanced TIL proliferation due to irradiated 618 tumor cells with that from irradiated A-431 cells in both serum-containing (a) and serum-free (b) media. A higher level of radioresistance of the A-431 cells resulted in a higher background for the assays in SFM.

DETAILED DESCRIPTION OF THE INVENTION

Figure 2A:
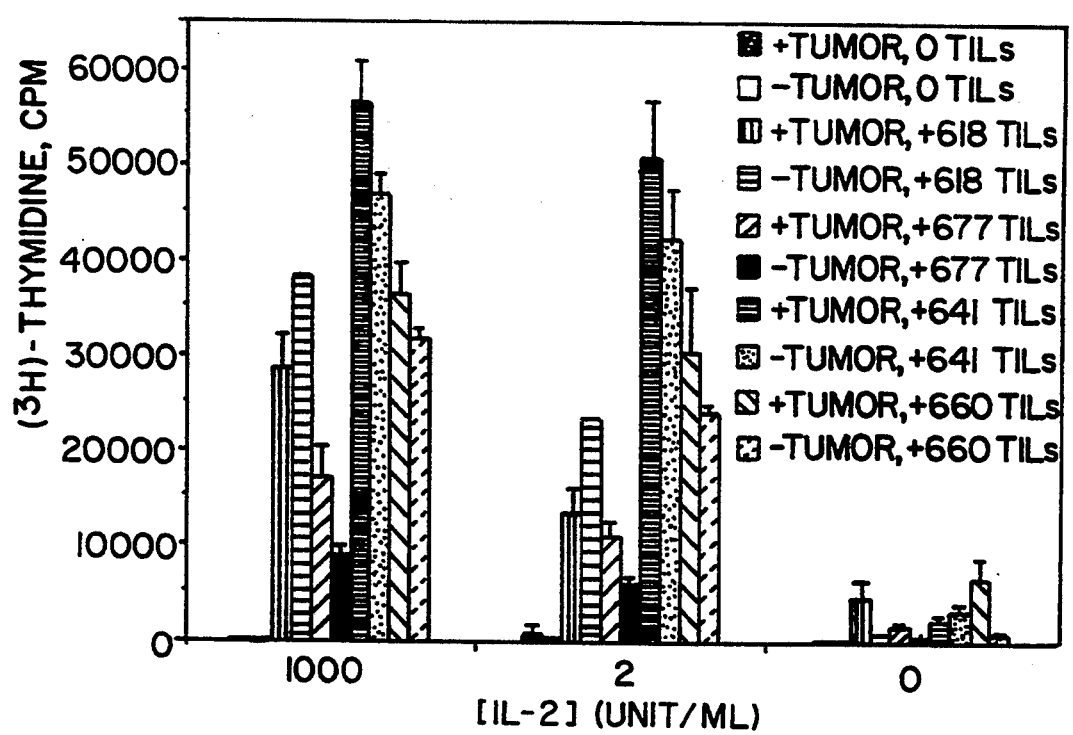
FIG. 2. Effect of irradiated 618 tumor cells on proliferation of four TIL lines at three IL-2 concentrations:1000,2, and 0 units/ml (a). (b) Expansion of right third of FIG. 2a: proliferation in the absence of IL-2.

Tumor-infiltrating lymphocytes (TILs) have shown in vivo antitumor efficacy in both animal and human studies. Functions thought necessary for antitumor activity include cytolysis, homing, and proliferation at tumor sites. TIL's which are T lymphocytes grown ex vivo directly from tumors, bear interleukin 2 (IL-2) receptors capable of transducing the IL-2 mitogenic signal. However, IL-2 is not normally synthesized by solid tumor cells. In order to explore the possible presence of T-cell mitogens of tumor origin, the present invention studied four TIL lines derived from four melanoma patients for their ability to use the environments of cultured tumor cell lines as mitogenic sources. The presence of four irradiated cultured human tumor cell lines, three of which were derived from the same melanoma patients as the TILs, were found to stimulate proliferation of human TIL's in the absence of IL-2. The observed proliferative stimulation by the fourth tumor line was due to secreted factor(s) as mitogenic activity was present in the serum-free tumor cell supernatant. Both immunologic analyses of this medium and proliferative assays in which TILs were stimulated with recombinantly lymphokine standards suggest the presence of a T-cell mitogen.

In one embodiment, the present invention relates to an oncoimmunin-lymphoid factor (preferably, a human tumor cell line factor) having the ability to stimulate human T-lymphocyte (preferably, a tumor infiltrating lymphocyte) mitogenesis in serum free medium.

In another embodiment, the present invention relates to a method of stimulating human T-lymphocyte (preferably, a tumor infiltrating lymphocyte) mitogenesis in a mammal (preferably, a human) comprising administering to the mammal the above-described oncoimmunin-lymphoid factor in an amount sufficient to stimulate human T-lymphocyte mitogenesis.

In a further embodiment, the present invention relates to an oncoimmunin-myeloid factor (preferably, a human tumor cell line factor) having the ability to induce myeloid differentiation in serum free medium.

In yet another embodiment, the present invention relates to a method of inducing myeloid differentiation in a mammal (preferably, a human) comprising administering to the mammal the above-described oncoimmunin-myeloid factor in an amount sufficient to induce myeloid differentiation.

In a further embodiment, the present invention relates to a pharmaceutical composition comprising the above-described oncoimmunin-lymphoid factor in an amount effective to stimulate human T-lymphocyte mitogenesis, and a pharmaceutically acceptable diluent, carrier, or excipient.

In a further embodiment, the present invention relates to a pharmaceutical composition comprising the above-described oncoimmunin-myeloid factor in an amount effective to induce myeloid differentiation, and a pharmaceutically acceptable diluent, carrier, or excipient.

The present invention is described in further detail in the following non-limiting examples (see Packard (1990) Proc. Natl. Acad. Sci. USA Vol. 87, pp. 4058–4062; Packard et al (April, 1991) Federation of American Societies of Exp. Biol., Atlanta, Ga. (abstract); Packard (1991) Biophysical Society of America (abstract); Packard (1990) Biophysical Society of America, Baltimore, Md. (abstract); Packard (1990) American Association of Cancer Research, Washington, D.C. (abstract); Packard et al (1990) Mitogenic stimulation of human tumor infiltrating lymphocytes by human tumor cell lines, Florence, Italia (abstract); Packard (1989) American Society for Cell Biology Houston, Tex. (abstract); Packard (1989) Hilton Head, S.C. (abstract); and Packard (1989) Berlin, W. Germany (abstract).

EXAMPLES

The following protocols and experimental details are referenced in the Examples that follow:

Materials

Dulbecco's modified Eagle's medium (DMEM) (4.5 g of glucose per liter) and Ham's F-12 medium were purchased from Flow Laboratories; AIM-V and RPMI 1640 media and fetal calf serum (FCS) were from GIBCO; insulin/transferrin/sodium selenite medium supplement was from Sigma; human albumin (Albutein) was from Alpha Therapeutic (Los Angeles); and [$^3$H]thymidine (6.7 Ci/mmol; 1 Ci=37 GBq) was from New England Nuclear. Recombinant human interleukins 4 and 6 (IL-4 and IL-6) and tumor necrosis factor $\alpha$ (TNF-$\alpha$) as well as neutralizing murine monoclonal antibody against human IL-6 (catalog 40028) were from Genzyme; rabbit anti-human IL-2 IgG antibody (catalog 40012) was from Collaborative Research; recombinant human transforming growth factor $\beta$ (TGF-$\beta$) was from R and D Systems; and IL-2 came from Cetus. Fluorescein- and phycoerythrin-labeled antibodies (anti-CD3, -CD4, and -CD8) were from Becton Dickinson. Fluorescein labelled CD-41 antibody was obtained from culture.

The clone of A-431 cells used in this study was from J. E. DeLarco (Monsanto), dog smooth muscle cells were from T. Innerarity (Gladstone Foundation, University of California, San Francisco), Madin-Darby canine kidney (MDBK) cells were from the American Type Culture Collection, and the 618, 677, and 660 tumor lines were established from human melanoma tumors by culturing in RPMI 1640/10% human serum. Four T-lymphocyte lines, TILs 618, 641, 660 and 677, were established from four human melanoma tumors as described (17). The tumor-derived TIL lines 618, 680, and 677 were all deposited according to the terms of the Budapest Treaty with the American Type Culture Collection (ATCC) of 12301 Parklawn Dr., Rockville, Md. 20852 USA on Feb. 4, 1994, and assigned Accession Numbers: CRL 11545, 11546, and 11547, respectively.

A bioreactor with a cartridge containing hollow fibers having a molecular-weight cutoff of 10 kDa [Cellco Advanced Bioreactors (Kensington, Md.)] was used for the large-scale culture of A-431 cells.

ELISA kits for IL-2, IL-4, and IL-6 were from Genzyme; a second ELISA kit for IL-2 was from Collaborative Research.

Q-Sepharose Fast Flow and Sephacryl S-300 resins and Mono-Q (HR 5/5) and Phenyl Superose (HR 5/5) fplc columns were purchased from LKB-Pharmacia. Precast SDS polyacrylamide (8–16% gradient and 12%) and isoelectric focusing (pH 3–10) gels were bought from Novex. Molecular weight and IEF standard were obtained from Sigma and Bio-Rad. A C4 reverse phase column (4.6×250 mm) was from SynChrom, Inc.

Human lymphocyte line, 660 TILs, was derived from a melanoma tumor. HL-60, HEL, and K562 cell lines were obtained from the FDA cell repository.

Culturing

All tumor lines were carried in DMEM 10% FCS, and the four TIL lines were in AIM-V supplemented with IL-2 at 1000 units/ml.

The serum-free medium (SFM) used for proliferation assays was a modification of a serum-free medium used for melanoma cells (18) with DMEM/Ham's F-12 at a 1:1 ratio substituting for DMEM alone.

The bioreactor cartridge was seeded with $\approx 5 \times 10^3$ A-431 cells in DMEM/10% FCS. After 3 weeks, the medium in the extracapillary space (ECSM) of the cartridge was switched to the SFM and the FCS concentration in the reservoir medium was lowered from 10% to 2%. The ECSM was drained daily from the cartridge, which was then filled with fresh SFM. The conditioned medium (ECSM) was then centrifuged, filtered (0.22 $\mu$m), and stored at 4° C.

Phenotyping

Staining was done at 4° C. for 30–60 min in Hank's balanced salt solution/10% FCS 0.02% $NaN_3$. Flow microfluorometric analyses were performed by using a Coulter EPICS flow cytometer.

Cellular Proliferation Assays

Tumor cells at $5 \times 10^4$ cells per cell were plated in 96-well flat-bottomed plates. Confluent cultures of tumor cells were irradiated (3000 rads) 1 rad=0.01 Gy) just before cocultivation with TILs. Lymphocytes were removed from IL-2 containing AIM-V and placed in the appropriate medium for bioassay 48 hr before commencement of proliferation assays. They were resuspended in SFM or DMEM/10% FCS at $1.25 \times 10^5$ lymphocytes per ml for cocultivation experiments and at $6 \times 10^5$ lymphocytes per ml for experiments in which soluble factors were being assayed; 200 $\mu$l of cell suspension was added per well. Cellular proliferation was determined in the presence of conditioned media and cytokines at the indicated concentrations. For experiments in which neutralization by an antibody was being measured, conditioned media were preincubated with the antibody at concentrations up to 10-fold the labeled neutralization capacity for 2.5 hr at 37° C. before the addition of cells.

After 24-or 48-hr stimulation, the level of lymphocyte proliferation was assayed by adding 0.5 $\mu$Ci of [$^3$H]thymidine to each well of a 96-well plate for 4 or 18 hr. A Skatron harvester was used to harvest the cells, and the radioactivity was counted by using an LKB $\beta$-plate reader. Each measurement was done in sextuplicate; each experiment was repeated at least three times.

The following assay conditions are critical in indentifying the tumor-derived activities described.

1. Two days prior to performing the assay T-cells must be removed from IL-2 containing medium and must be placed in serum-free medium. Use of cells after one or three days will not lead to successful detection of activity. This optimization time is not obvious to a qualified researcher in this field since the routine procedure is to simply wash the cells and to use them immediately or at one day.

2. Optimization of mitogenic activity is at 24 hours after commencement of assay.

3. The data suggests that this is a unique activity in that under serum-free conditions, no other tumor-derived factor is capable of stimulating T-cell growth.

Thymidine incorporation assays for 660 TILs were performed. For hematopoietic lines, i.e., HL-60, HEL, and K562, the cells were carried in RPMI with 10% fetal calf serum. Forty-eight hours prior to commencement of proliferation assays, cells were removed from serum-containing medium by washing twice in serum-free medium and culturing for this 48 hour interval in the latter medium. For proliferation assays the concentration of hematopoietic cells was $2.7 \times 10^5$ cells/ml.

Protein Purification

Serum-free conditioned medium from A431 cells which were grown in a bioreactor was diluted 10-fold with 5 mM potassium phosphate buffer, pH 7.5. This material was loaded onto a Q-Sepharose Fast Flow column (4.5 $\times$ 17 cm) which had been equilibrated with a 15 mM potassium phosphate buffer, pH 7.5. The sample volume ranged from two to four liters. The column was then washed with 1 liter of 15 mM phosphate buffer, pH 7.5 after the sample loading was completed. This was followed by elution with 400 ml of a 15 mM phosphate buffer containing 35 mM sodium chloride. Gradient elution with sodium chloride starting with 35 mM and ending with 200 mM sodium chloride in 15 mM potassium phosphate buffer, pH 7.5 was run. An additional one liter elution was carried out with 15 mM phosphate buffer containing 200 mM sodium chloride. Fractions of 150 drops each were collected throughout the gradient. In bioassays which were performed on fractions 1 through 200 the eluted material was diluted 7.5-fold.

The first bioactive domain, ca. fractions 30 through 60, coeluted with the soluble epidermal growth factor (EGF) receptor, previously described as Oncoimmunin-M or early eluting Q-Sepharose peak. The second bioactive domain, ca. fractions 110–135, has previously been described as Oncoimmunin-L or late eluting Q-Sepharose peak.

Active fractions from the EGF receptor domain (Oncoimmunin-M) from the Q-Sepharose column were pooled and placed in a Filtron filter unit with a cutoff of 10 kDaltons; here concentration and equilibration into buffer A (50 mM phosphate, pH7 plus 1.7M ammonium sulfate) were carried out. This material (ca. 50 ml) was then loaded onto a Phenyl Superose column. Elution was carried out by a series of step gradients (35, 40 and 100% B) of buffer B (50 mM phosphate, pH 7).

The material from the 100% B step of the Phenyl Superose column was loaded onto a Sephacryl S-300 column (2.5 $\times$ 100 cm). Elution was carried out using a 15 mM phosphate buffer, pH 7.4. Fractions of 85 drops were assayed after a 1 to 7.5-fold dilution.

Fractions from the second bioactive domain of the Q-Sepharose column (Oncoimmunin-L) were pooled, concentrated in a Filtron filter unit, and then loaded onto a Sephacryl S-300 (2.5 $\times$ 100 cm) column. Elution was performed with a 15 mM phosphate buffer, pH 7.4. Active fractions were concentrated, equilibrated in a 25 mM Tris buffer, pH 7.48, and loaded onto a Mono-Q column. Elution was performed with a gradient using 25 mM Tris, pH 7.48 plus 0.50 M sodium chloride. Active fractions from the Mono-Q column were injected onto a $C_4$ hplc column equilibrated with water containing 0.05% trifluoroacetic acid (TFA). Elution was performed with an increasing gradient of buffer B which was acetonitrile containing 0.05% TFA. With a flow rate of 1 ml/minute throughout the following gradient was run: at time(t)=0 minute, 0% B; at t=30, 36% B; at t=70, 60% B; at t=80, 90% B. All segments of the gradient were linear.

EXAMPLE 1

Growth Characteristics of TILs

In FIG. 1a TIL line 618 cells are shown growing in large clusters in suspension. In contrast, in FIG. 1b these TILs in the presence of a monolayer of cell line 618 tumor cells are seen growing in tight apposition to the tumor cells; the absence of large clusters of lymphocytes suggests the predominance of cellular heterophilia over homophilia. Thus, tumor cells induced a striking change in the morphology of TIL-TIL interactions. The question of whether this morphologic alteration was due to an interchange of biologic signals between the two different cell types was addressed.

TABLE 1

| TIL | Phenotypes of TILs measured by flow cytometry | | |
|---|---|---|---|
| | CD3+ % | CD8+ % | CD4+ % |
| 618 | 97 | 83 | 12 |
| 677 | 99 | 93 | 3 |
| 641 | 97 | 19* | 95 |
| 660 | 98 | 88 | <3 |

*Nineteen percent of 641 TILs were double-positive for both CD8 and CD4; none was singly positive for CD8.

EXAMPLE 2

TIL Proliferation

Figure 2B:
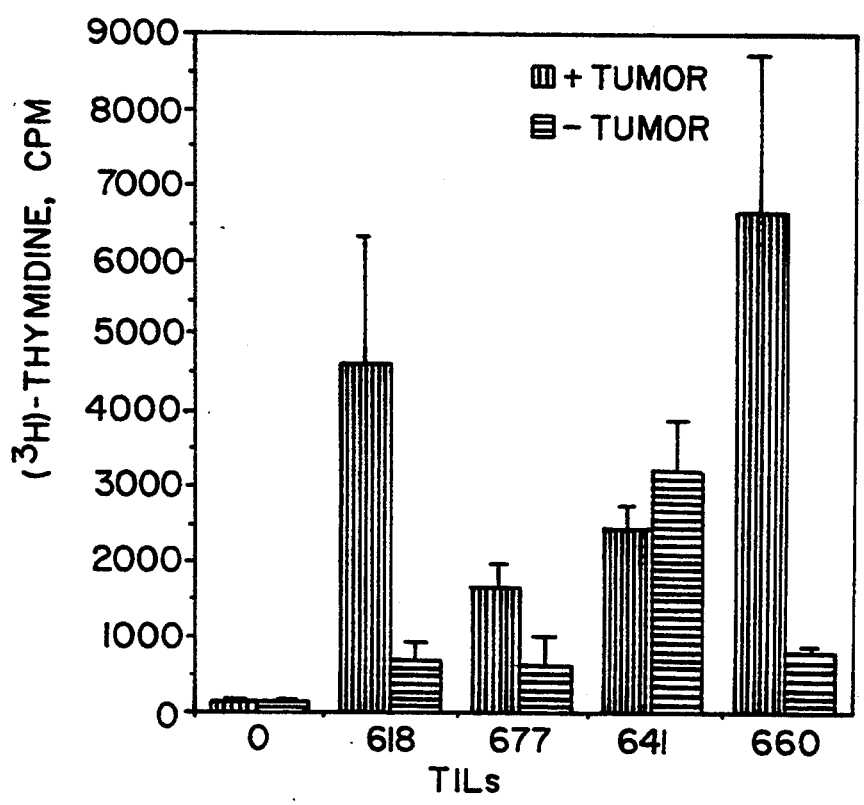

To determine whether a tumor cell line can stimulate growth of TILs the cellular proliferation rates of TIL lines derived from four (618, 677, 641 and 660) patients were determined with and without an irradiated tumor cell line established from one of the patients (618). Because all four TIL lines had a culture history of IL-2 dependence, the initial set of experiments was done in the presence of IL-2 (1000 and 2 units/ml) as well as in its absence. As seen in FIG. 2a with IL-2 present at either 1000 or 2 units/ml, 618 tumor cells did not enhance by >2 SD [$^3$H]thymidine incorporation into DNA of any of the four TIL lines except for 677 at 2 units of IL-2 per ml; the latter was barely significant because the observed enhancement was by just 2 SD. In contrast, FIG. 2b shows that without IL-2, proliferation of both 618 and 660 TIL lines was dramatically increased when irradiated 618 tumor cells were present. The response of the 677 TIL line was again marginally significant. Presence of tumor cells had no effect on the proliferation of the 641 TILs, a cell line with a phenotype of 100% CD4+. The three other TIL lines (618, 660, and 677) are composed of, at least, 80% CD8+cells. Hence, lymphocyte proliferation assays suggested the proliferative potentiation of tumor cells for CD8+lymphocytes in the absence of IL-2.

EXAMPLE 3

Tumor Potentiation

To determine whether tumor stimulation in the absence of IL-2 was independent of serum factors, proliferation assays were done in parallel in SEM and DMEM/10% FCS. FIG. 3 indicates that the proliferation levels of both 618 and 660 TILs were significantly increased by 618 tumor cells whether or not serum was present. The proliferation of 677 TILs was marginally affected—i.e., by not >2 SD in either medium. 641 TILs showed statistically insignificant changes upon addition of tumor cells. Hence, the results suggested that the enhancement of proliferation of TILs by 618 tumor cells was independent of serum-derived factors.

EXAMPLE 4

Enhancement of TIL Proliferation

Proliferation of TIL 660, the best responder to tumor cell-enhanced proliferation, was measured in the presence of two additional melanoma lines, 660 and 677, both established from the respective TIL patients. Data listed in Table 2 show a similar 3- to 4-fold increase in the proliferative response of 660 TILs to the presence of irradiated 660 or 677 tumor lines, seen with the irradiated 618 tumor line.

EXAMPLE 5

Potentiation Specificity

Because melanomas derive from the neural crest, cells of a line not derived from this embryologic origin—i.e., the A-431 cell line, which was originally derived from an epidermal carcinoma, were tested for ability to potentiate TIL proliferation in both serum-containing and serum-free media. FIG. 3 shows that irradiated A-431 cells potentiated proliferation of all four TIL lines in serum (FIG. 3a) and showed effects similar to 618 tumor cells in SFM (FIG. 3b).

EXAMPLE 6

Transformed Cell Line Specificity

In contrast to the melanoma and A-431 cell lines tested, irradiated dog smooth muscle cells and MDBK cells, two untransformed cell lines, did not potentiate TIL proliferation. Although this fact, along with stimulation by the murine melanoma B16 line, supports the concept of TIL stimulation by transformed and not normal cells, it would be premature to make this generalization, as all cell lines by virtue of their ability to survive ex vivo for extended times have acquired some traits of a transformed phenotype. Validation of tumor specificity awaits determination of the presence or absence of a purified factor in fresh uncultured cells.

EXAMPLE 7

Secreted Factors

Figure 4:
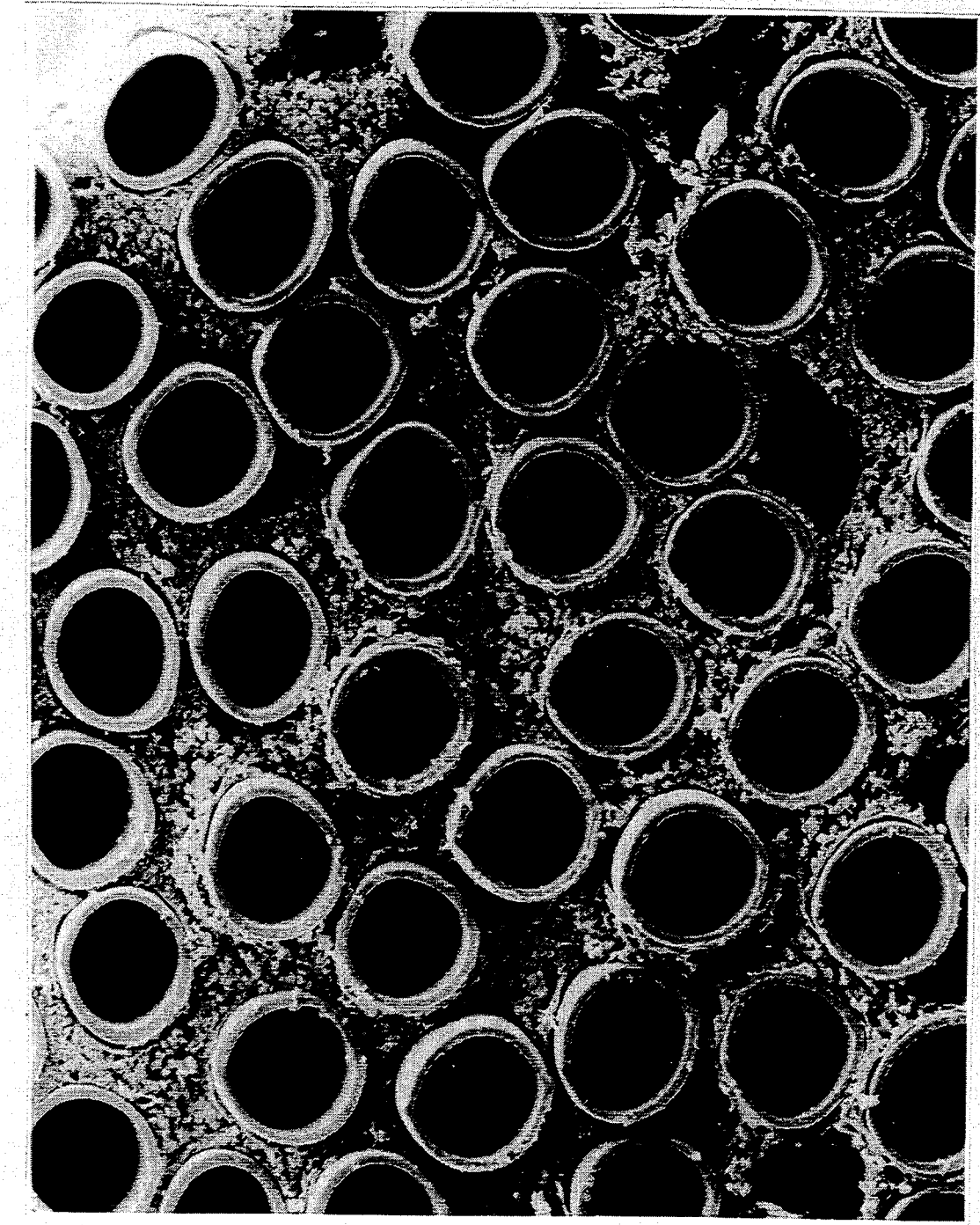
FIG. 4. Scanning electron micrograph of A-431 cells grown in hollow fiber bioreactor. Dark insides of hollow fibers that contain reservoir medium—i.e., DMEM/2% FCS—are separated from extracapillary space containing A-431 cells by a membrane with a 10-kDa cutoff (x60).

A scanning electron micrograph shows A-431 cells in the hollow fiber cartridge in cross section (FIG. 4). Tumor cells were only seen in the space outside the hollow fibers. The membranes lining these fibers had a molecular mass cutoff of 10 kDa; hence, any factors secreted by the tumor cells with a molecular mass >10 kDa were retained in the ECSM. The medium that circulated inside the hollow fibers was composed of DMEM/2% FCS and was designated as the reservoir. The ECSM was drained daily and assayed for bioactivity.

TABLE 2

| Proliferation of 660 TILs in SFM in the absence and presence of irradiated melanoma cells lines | |
|---|---|
| Tumor cell line | [$^3$H]Thymidine cpm |
| None | 355 ± 54 |
| 618 | 1661 ± 57 |
| 677 | 1289 ± 52 |

TABLE 2-continued

Proliferation of 660 TILs in SFM in the absence and presence of irradiated melanoma cells lines

| Tumor cell line | [$^3$H]Thymidine cpm |
|---|---|
| 660 | 1182 ± 154 |

Background counts for tumor alone have been substracted.

Figure 5A:
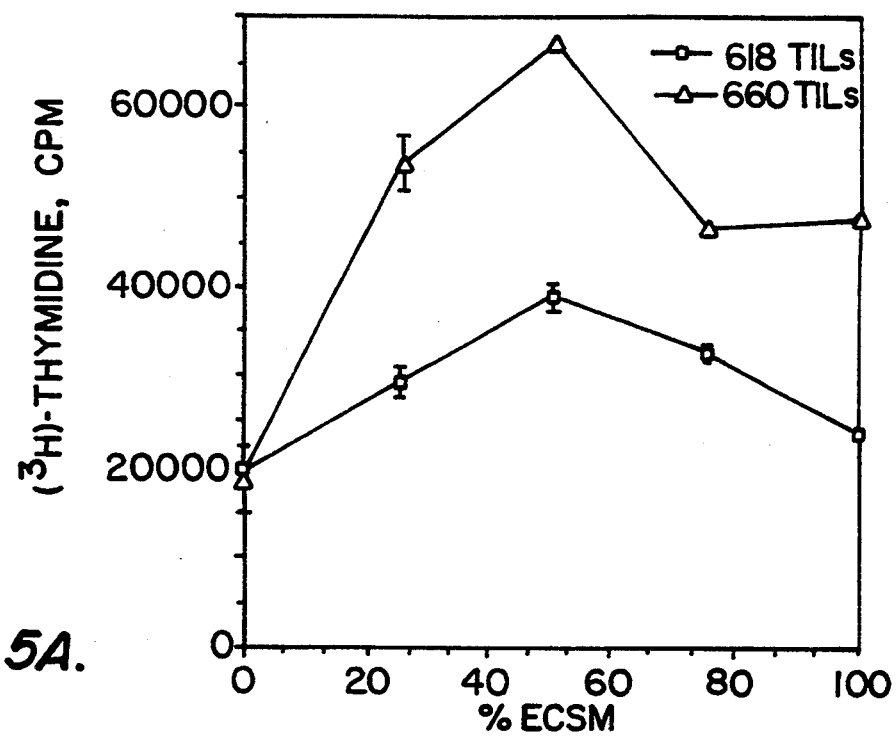
FIG. 5. Proliferation assays with serum-free supernatants from bioreactor ECSM secreted by A-431 cells (a) and serum-containing medium of reservoir—i.e., dark insides of hollow fibers shown in FIG. 4(b).

Rates of [$^3$H]thymidine incorporation into both 618 and 660 TILs as a function of increasing concentrations of ECSM are plotted in FIG. 5a. There is a dose-dependent increase in proliferative activity up to the assay composition of 50% ECSM for both 618 and 660 TILs. Above this level both curves fall off. These declines may be due to the absence of nutrients in the spent ECSM or the presence of the inhibitory factor(s). Additionally, these curves may also represent behavior similar to that of other known mitogens, for which at high concentrations proliferative levels are submaximal. In support of the latter hypothesis—when partially purified material was used as the stimulus, the dose-response curve was U-shaped with the maximum observed at $\approx 1$ mg of protein per ml.

Figure 5B:
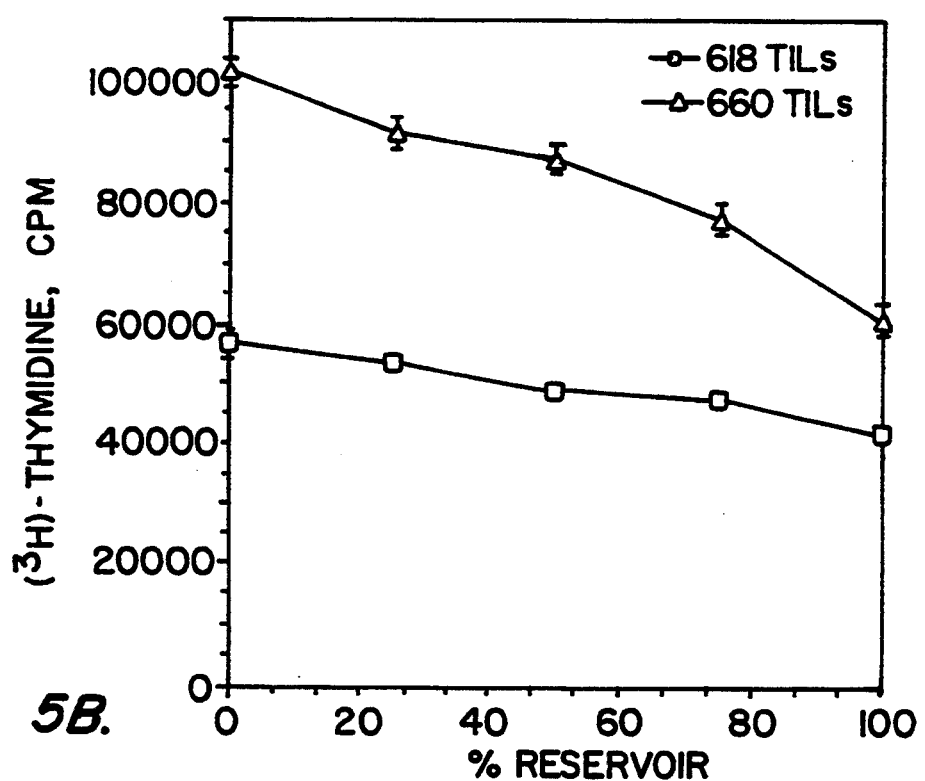

In FIG. 5b rates of [$^3$H]thymidine incorporation into both 618 and 660 TILs as a function of increasing concentrations of reservoir medium are plotted. No stimulatory activity was detectable. Thus, molecular mass of the mitogenic factor(s) must be, at least, 10 kDa as no mitogenic activity was associated with factor(s) secreted into the reservoir.

EXAMPLE 8
T-Cell Mitogens

To determine whether the mitogenic activity present in ECSM was due to factors that have previously been shown to have direct mitogenic activity for T cells, three ECSM samples collected at 2-week intervals were tested for IL-2, IL-4, and IL-6 by ELISA.

The presence of neither IL-2 (using kits from the two indicated companies) nor IL-4 was measurable at or above detection levels for these two lymphokines—i.e., 0.4 Cetus unit per ml and 90 pg/ml, respectively. At these two respective concentration levels no significant proliferative activity above background was detected. However, IL-6 was found to be present at 2 ng/ml; the presence of IL-6 in A-431 cell supernatants has been reported (19).

To ascertain whether IL-6 could be a mitogen for TILs under the conditions used in this study [$^3$H]thymidine incorporation was measured after culturing 660 TILs for 24 hr in the presence of IL-6 a; concentrations ranging from 0.01 to 20 ng/ml; no [$^3$H]thymidine incorporation background was measured. Furthermore, the presence of a neutralizing monoclonal antibody against IL-6 had no effect one stimulation of [$^3$H]thymidine incorporation inducted by ECSM, whereas mitogenic stimulation by IL-2 standards up to 100 units/ml was completely inhibited by the anti-IL-2 antibody used.

Lacked of mitogenic activity for 660 TILs was also seen for TGF-$\beta$ ($1 \times 10^{-7, -8, -9, -10, -11, and -12}$M) and TNF-$\alpha$ (1, 10, and 100 ng/ml). In all experiments IL-2 and ECSM served as positive controls.

The idea that the tumor environment contains lymphocytes that may exhibit antitumor activity was the basis for using lymphocytes expanded in culture as therapeutic agents (1-14). Much work supports the concept that an immune response is initiated against tumors via direct tumor cell-lymphocyte contact, followed by the secretion of factors mitogenic for lymphocytes from several immunocyte sources. However, the possibility of tumor cells providing a mitogenic stimulus for lymphocytes in the form of secreted factors has not been well explored. Thus, the objective of this work was to determine whether tumor cells could secrete factor(s) mitogenic for lymphocytes.

Figure 1a, which shows TILs growing in the presence of IL-2, is typical of cultures of activated lymphocytes—i.e., clusters of cells in suspension. In contrast, in the presence of mono-layers of tumor cells TILs have a spread appearance (Figure 1b). To determine whether the observed apposition between TILs and tumor cells was part of an immunostimulatory environment, proliferation of four TIL lines was compared in the presence and absence of irradiated tumor cells. In the presence of IL-2 addition of irradiated culture 618 tumor cells did not significantly affect mitosis of the four TIL lines tested (FIG. 2a), However, in the absence of IL-2 (FIG. 2b) these tumor cells dramatically increased the proliferation rates of two TIL lines, 618 and 660, and increased less significantly the rate of a third, 677. Thus, cultured tumor cells can support T-cell mitogenesis independently of IL-2. This fact may be essential in understanding the observed disparity in phenotypic profiles of TIL cultures at the stage of reinfusion onto patients with those of the starting populations (15, 20). That is, because receptors for IL-2 are present on virtually all activated T cells (21), the T cell population that will grow ex vivo in the constant presence of this lymphokine is strongly biased toward those cells capable of transducing and using the IL-2 signal most cells capable of transducing and using the IL-2 signal most efficiently. Hence, factors from the tumor environment, which may be essential for maintenance of lymphocytes with antitumor activity, may not be retained in long term cultures in which all tumor cells have died and the only exogenous cytokine is the pan T-cell mitogen IL-2.

In the present study the observed mitogenic stimulation of TILs by irradiated tumor cells was shown to be of cellular origin and not from the serum, as indicated by FIG. 3. In addition to the tumor line established from patient 618, data in Table 1 show that tumor lines from two other melanoma patients, 677 and 660, were similar in their ability to enhance proliferation of 660 TILs in SFM. Thus, the presently reported mitogenic T-cell stimulation by tumor cell lines, all of which were derived from unrelated patients, is clearly not the major histocompatibility complex-restricted.

To determine whether tumor cell-induced lymphocyte mitogenicity is characteristic of tumors of a specific embryonic origin, such as the neural crest, which includes melanomas a well as neuroblastomas, a cell line derived from a tumor of epidermal carcinoma origin, the A-431 line was used as a source of potentiation of TIL proliferation. Data indicating that A-431 cells can serve as a superior mitogenic source for TILs in serum (FIG. 3c) and equivalently to the 618 melanoma line in SFM (FIG. 3b) suggest that this type of immunocyte stimulation may be broadly prevalent.

Proof that activity mitogenic for TILs is secreted by A-431 cells was confirmed by the activity in the ECSM (FIG. 5a). These dose response curves indicate the presence of cytokines that exhibit behavior similar to that of other known mitogens, where submaximal proliferative levels have been measured at high concentrations. The absence of IL-2 and IL-4 by ELISA and the lack of proliferative stimuli from IL-6, TNF-a, and TOF-B under the experimental conditions used suggest the presence of a direct T-cell mitogen not previously characterized.

In conclusion, tumor cell lines can increase the proliferative potential of TILs in the absence of IL-2. The molecule (s) responsible for this activity may be essential components of the biochemical basis of immunogenicity observed in vivo and require further characterization.

EXAMPLE 9

Oncoimmunins

Factors named Oncoimmunin-Lymphoid (L) and Oncoimmunin-Myeloid (M) have been separated using Q-sepharose.

1. Oncoimmunin-L (late eluting Q-Sepharose peak): In vitro data which show this factor to be a T-cell mitogen suggest that is may be useful as an immunotherapeutic agent in both the laboratory and in the clinic. Specifically, it allow ex vivo expansion of T cells with retention of biologic characteristics for therapeutic usage. In addition, administration of this factor to patients may enhance immunologic response and maintenance of immunosurveillance of patients.

2. Oncoimmunin-M (early eluting Q-Sepharose peak): In vitro data indicate this factor's ability to inhibit growth and induce differentiation of three myeloid leukemic cell lines, i.e., HL-60, K562, and HEL. This factor may be useful in treating bone dysfunctions (specifically, bone marrow and bone morphogenesis dysfunctions). It may be useful alone or in combination with other colony stimulating factors and interleukins. In addition, it can be used to reduce secondary malignancy due to long-term treatment with carcinogenic chemotherapeutic agents.

Both factors, together or alone, may be used to identify in vitro cells that may have in vivo therapeutic efficacy.

Figure 6A:
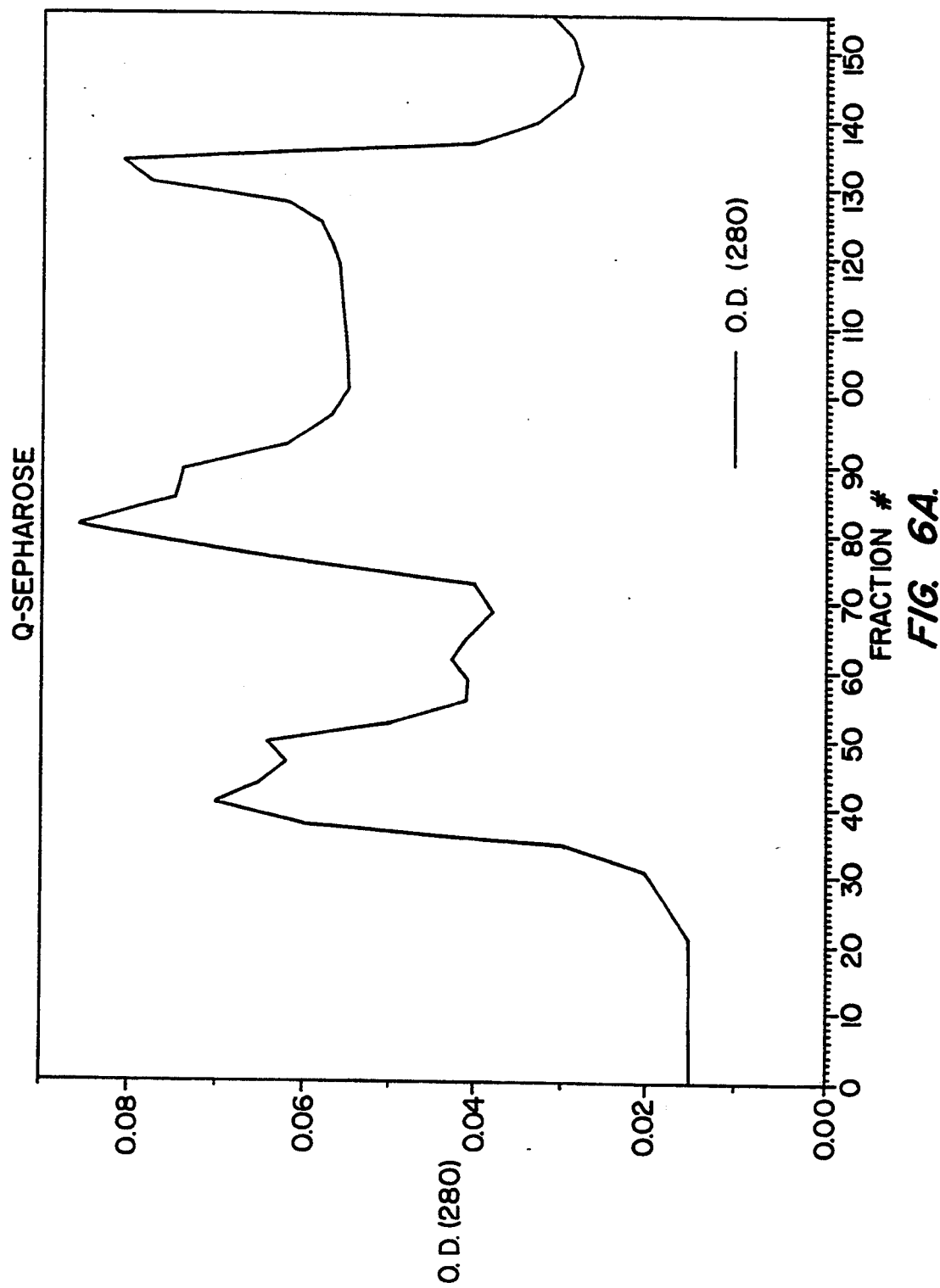
FIG. 6. Q-Sepharose chromatography a) Protein elution profile b) biological activities of Q-sepharose chromatography fractions.
Figure 6B:
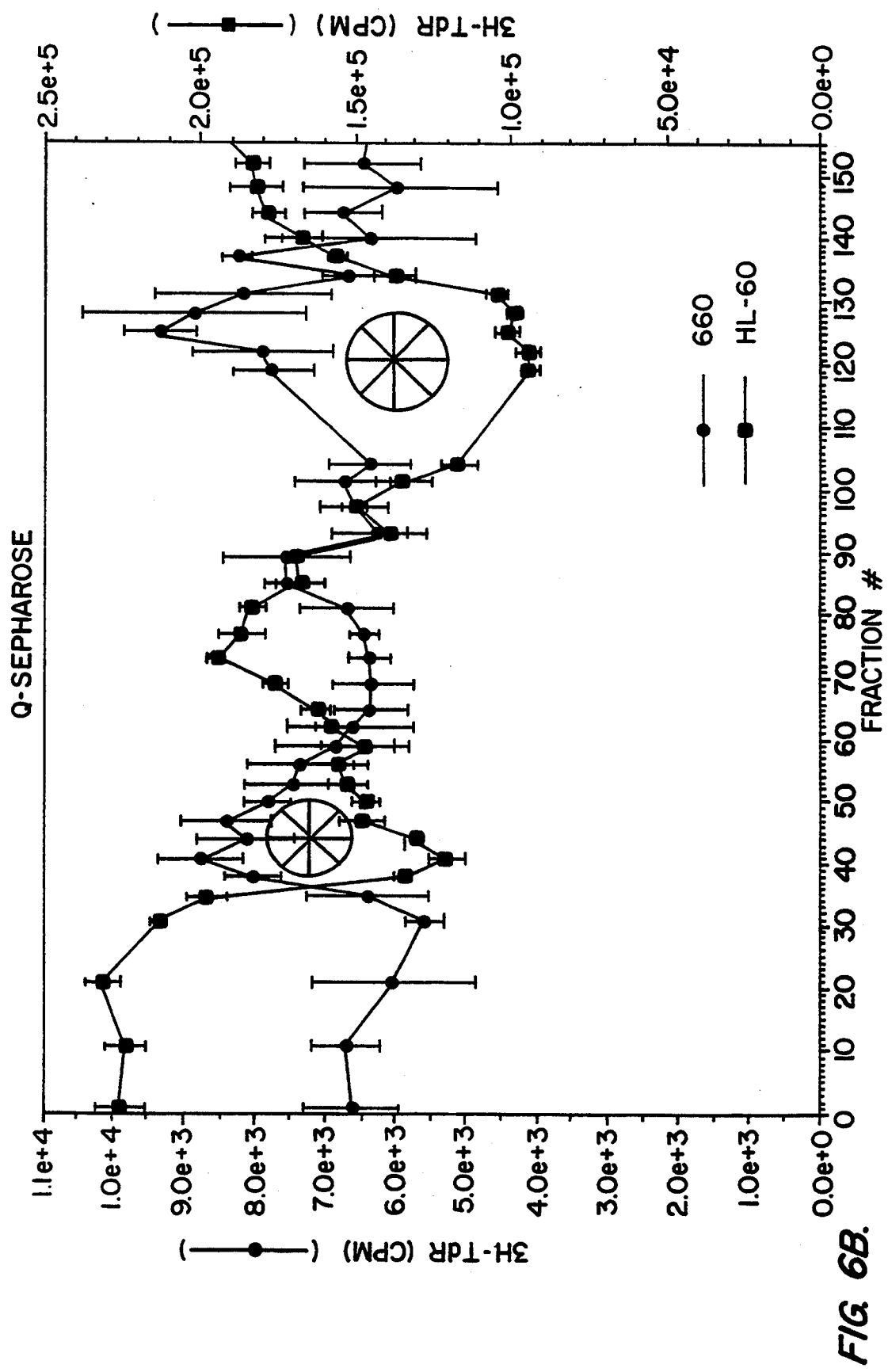
Figure 7:
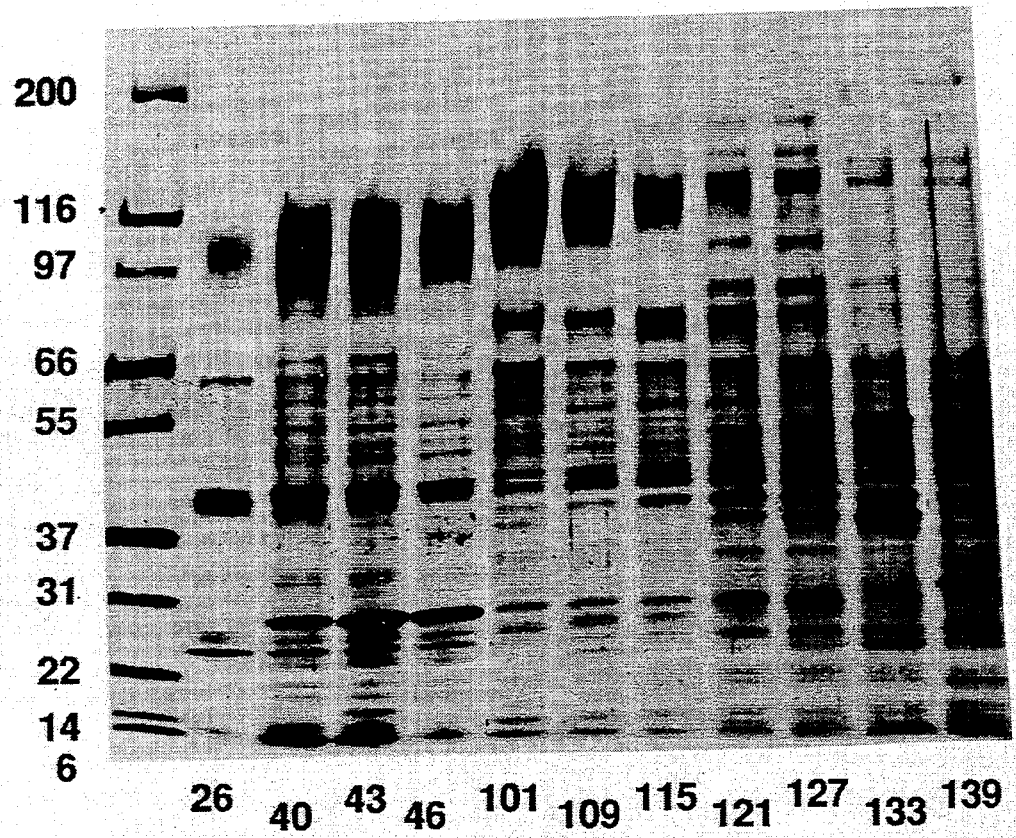
FIG. 7. SDS-PAGE showing protein composition.

Results from Q-Sepharose chromatography are shown in FIGS. 6a and 6b. Two domains of bioactivity were observed in fractions from Q-Sepharose as indicated in FIG. 6b. As the major protein in the first domain (fractions 30–60), named Oncoimmunin M, is the EGF receptor, as confirmed by Western blotting, EGF binding, and amino acid sequence analysis, this was name the EGF receptor domain. The second domain consisted of fractions ca. 110–135. Protein composition is shown by the gels in FIG. 7.

Figure 8:
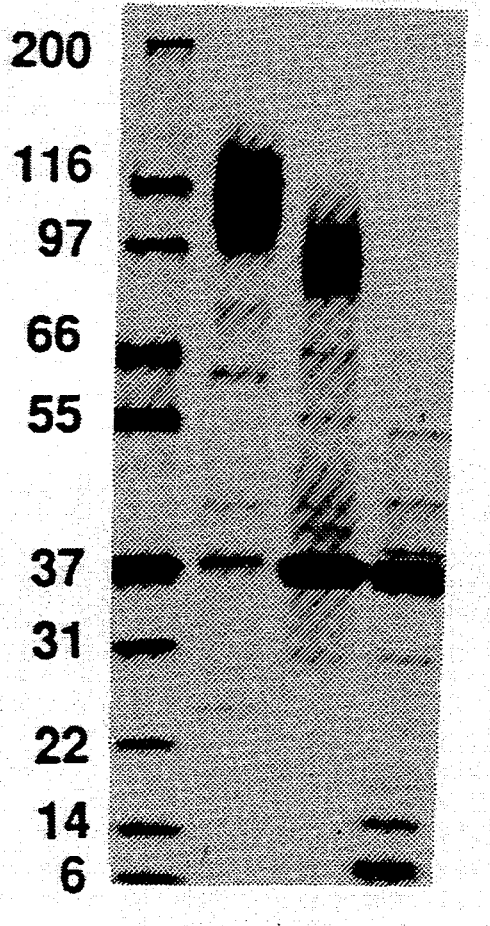
FIG. 8. Phenyl Superose.

FIG. 8 shows the gel from the three elution steps from the Phenyl Superose column.

Figure 9:
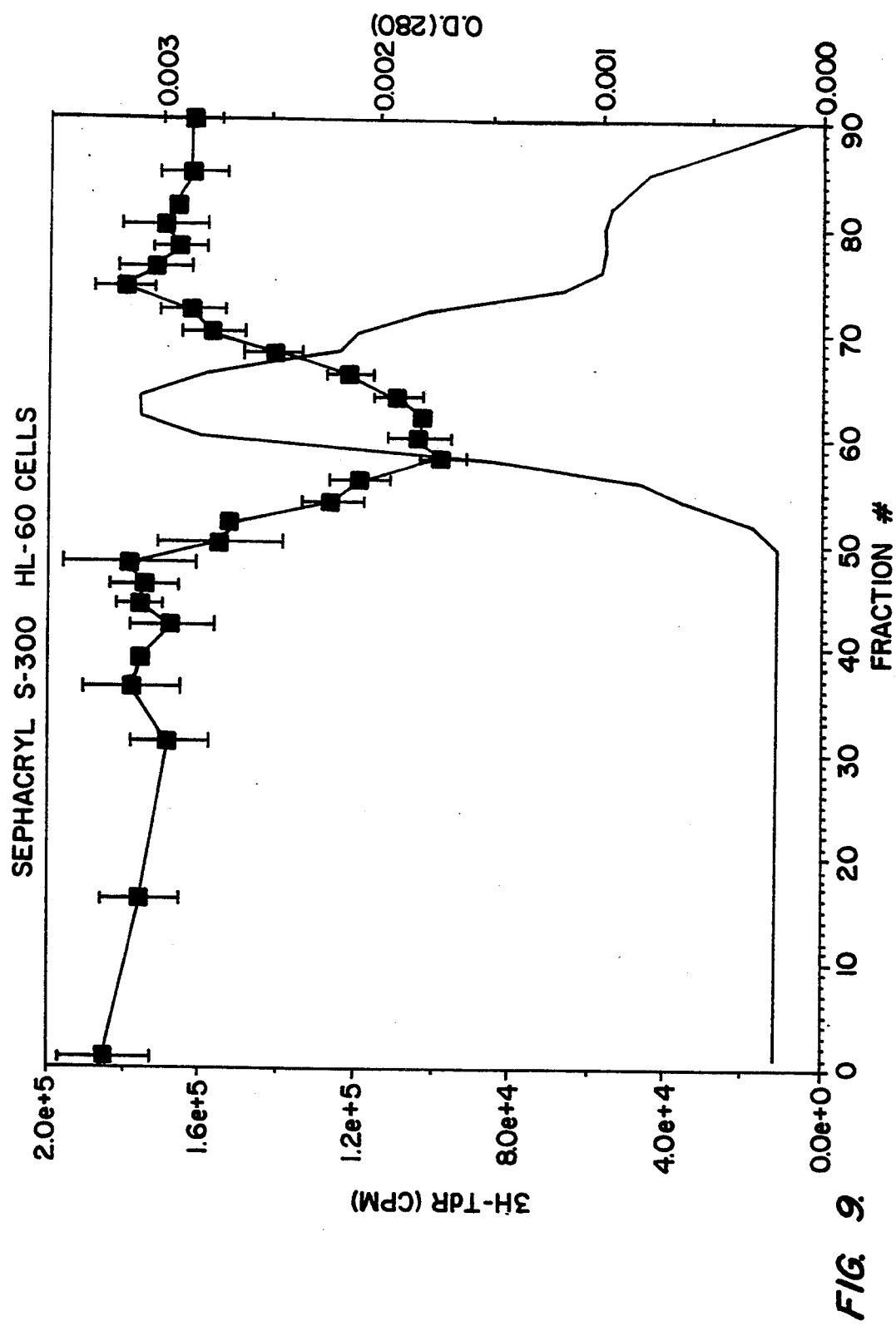
FIG. 9. Sephacryl S-300.

FIG. 9 shows results of fractions from the Sephacryl S-300 column of post-Phenyl Superose active material using the inhibition of thymidine incorporation into HL-60 cells as a measure of bioactivity.

Figure 10:
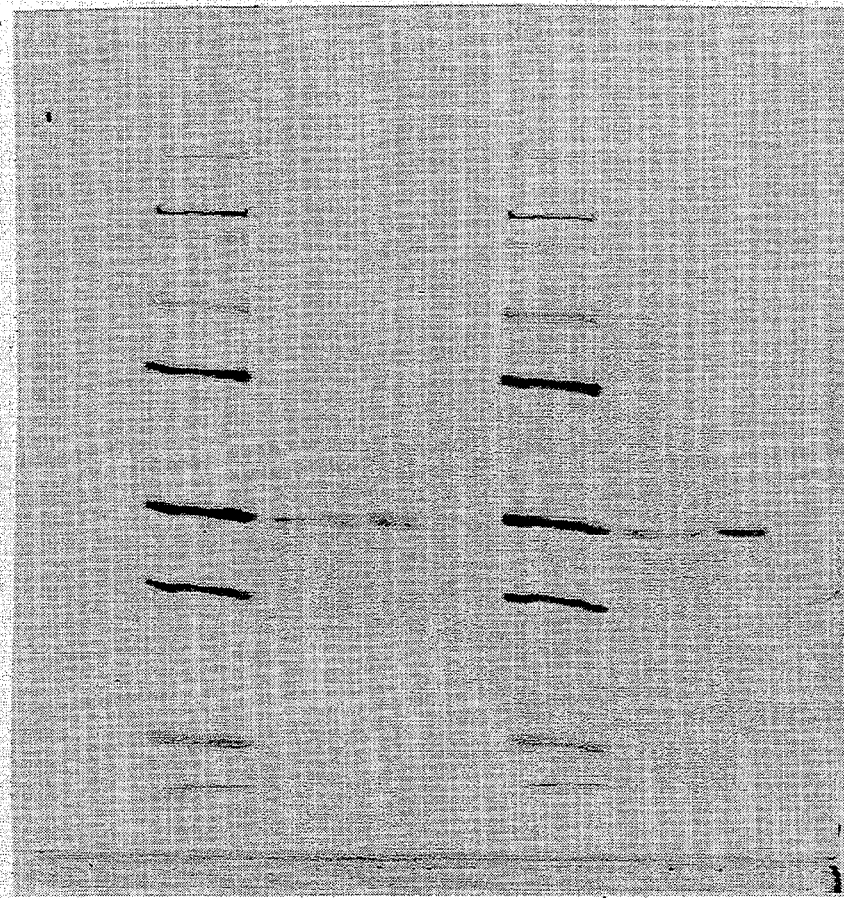
FIG. 10. Gels of fractions with highest bioactivity.

FIG. 10 shows gels from the domain (fractions 59–61) with highest bioactivity. The bioactive material runs at a molecular weight of ca. 36 kDaltons under both reducing and nonreducing conditions.

Figure 11:
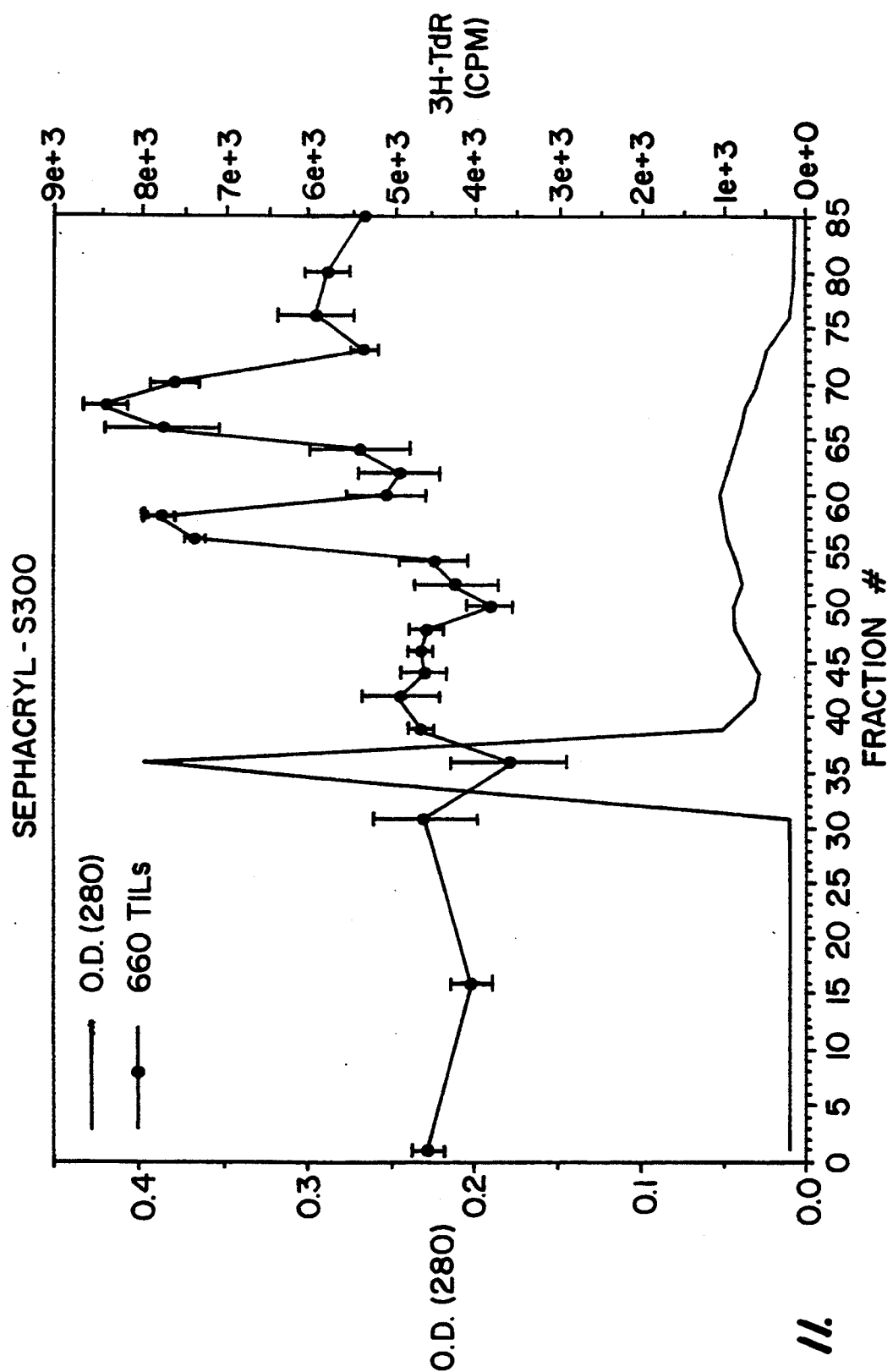
FIG. 11. Sephacryl S-300
FIG. 12. Mono-Q column.

FIG. 11 shows results from the Sephacryl S-300 column of material from the second Q-Sepharose (Oncoimmunin-L) domain. Using the stimulation of thymidine incorporation into 660 TILs as an indicator two domains of activity appeared: fractions 48–51 and 66–73.

Figure 12:
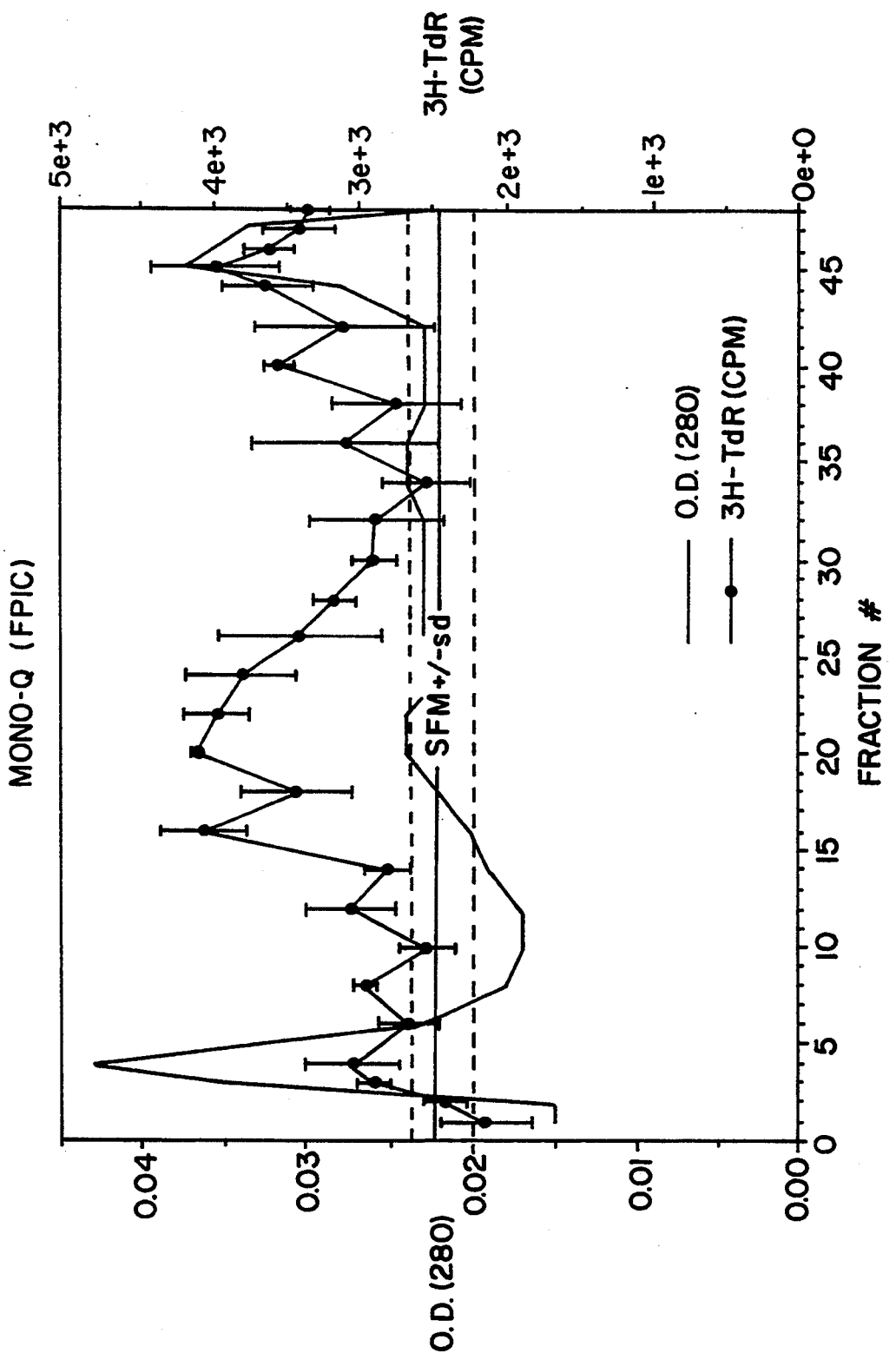

FIG. 12 shows results from chromatography of fractions 66–73 from the previous Sephacryl S-300 column (Oncoimmunin-L) onto the Mono-Q column.

Figure 13:
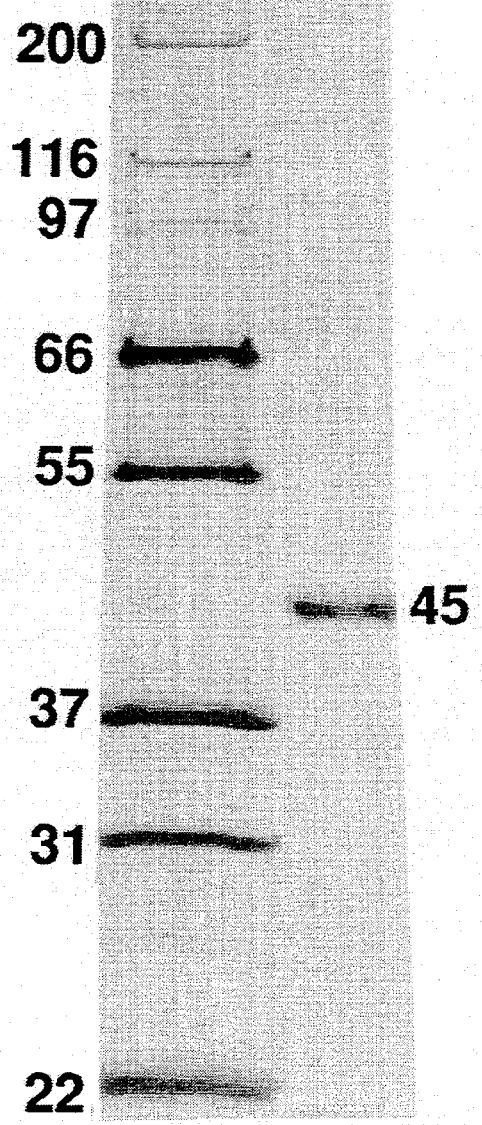
FIG. 13. C$_4$ Reverse Phase HPLC
FIG. 14. Histograms obtained by labeling HL-60 cells.

FIG. 13 shows the SDS-PAGE gel of material obtained after the $C_4$ reverse phase column. The material runs at a molecular weight of ca. 45 kDaltons.

FIG. 14 shows histograms obtained by labeling HL-60 cells with phycoerythrin-labeled CD-11b antibody. Data from control cells are indicated by the dotted line and from cells that had been incubated with Oncoimmunin-M for 2 days are by the dashed line.

Figure 15A:
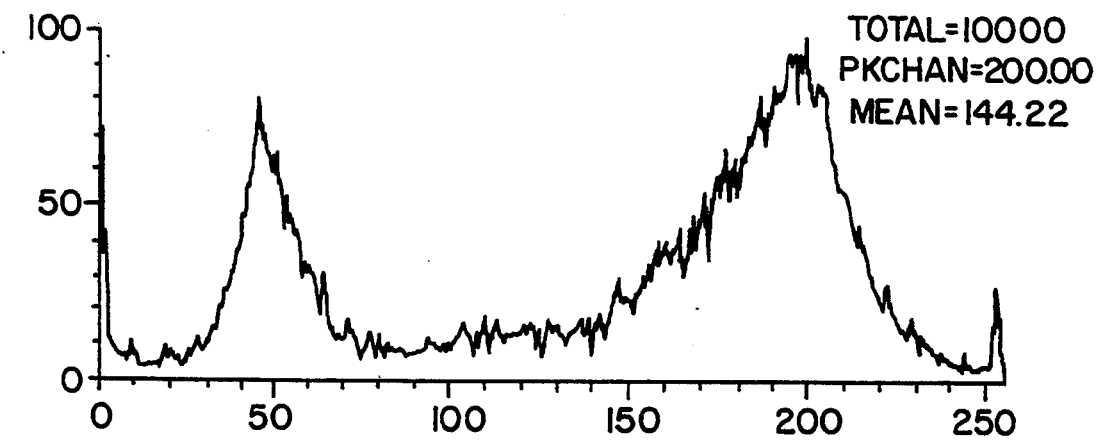
FIG. 15. Data from HL-60 cells incubated with CD-41-FITC antibody.
Figure 15B:
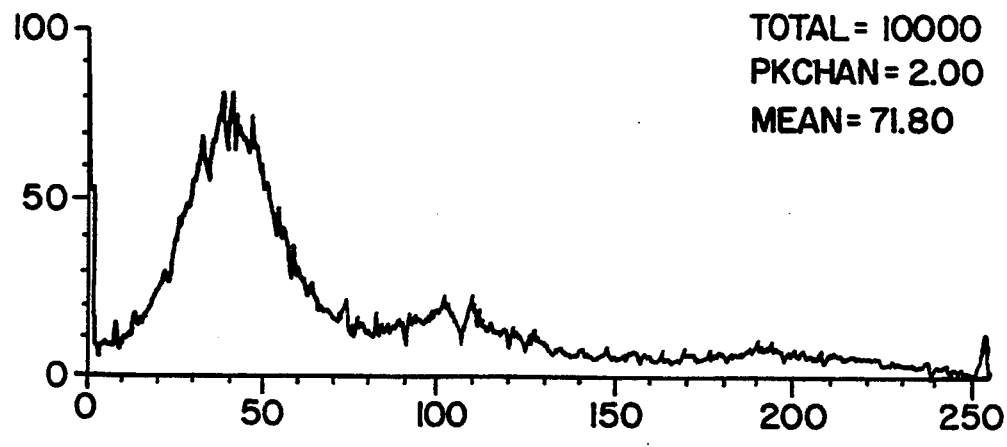
Figure 16:
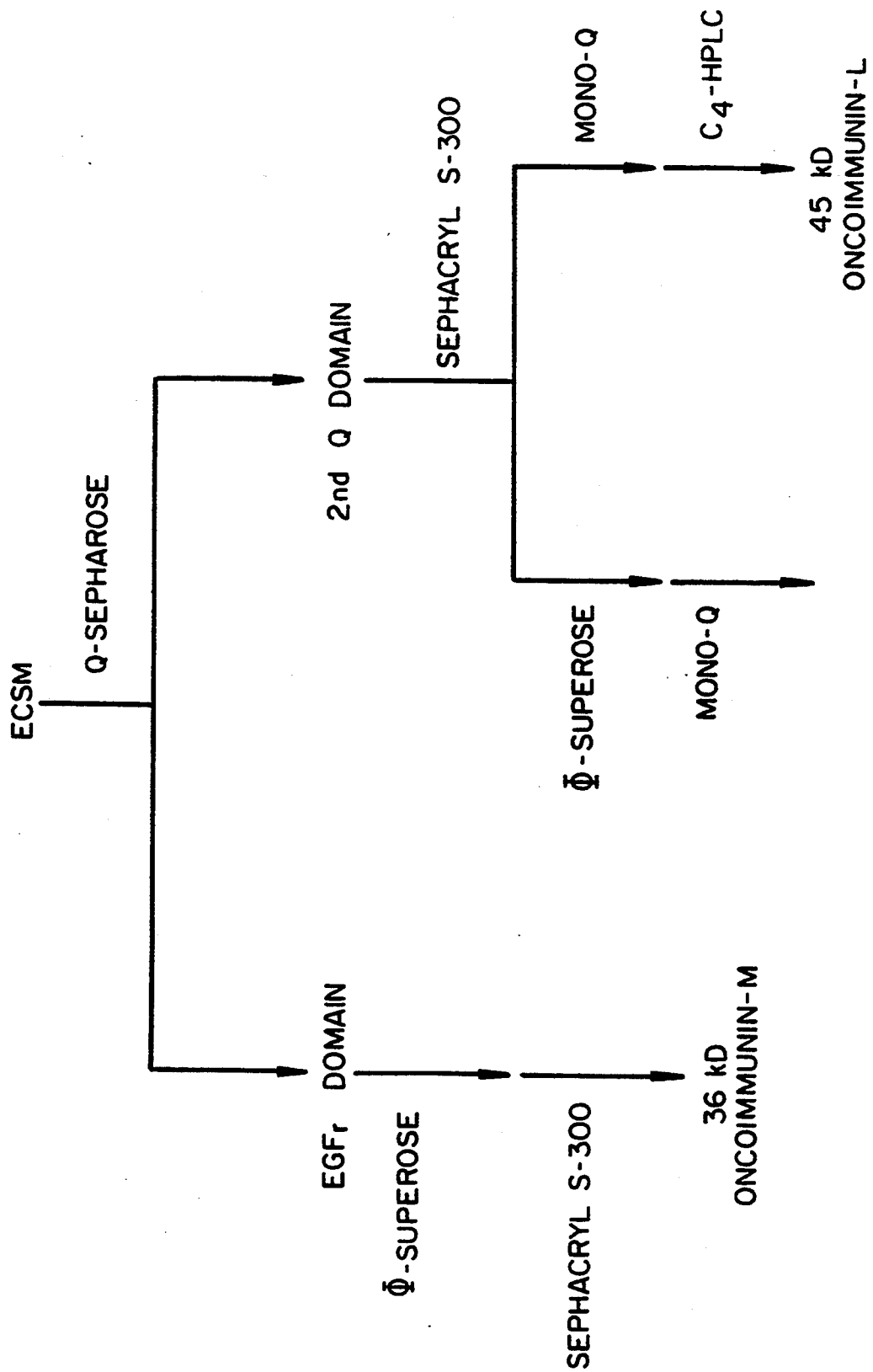
FIG. 16. Purification flow diagram.

FIG. 15 shows data from HL-60 cells that had been incubated with CD-41-FITC antibody (a) after two days treatment and (b) control cells. FIG. 15a shows increase in CD-41 on HL-60 cells which have been treated 2 days with the factor.

EXAMPLE 10

Differentiation of leukemic cell lines

HL-60, K562, and HEL cells are removed from RPMI medium containing 10% fetal calf serum and washed twice in the serum-free medium used for oncoimmunin-L. They are incubated for two days in this medium. The bioassay is then run under the following conditions: $0.6$–$2.4 \times 10^5$ cells/200λ/well of a 96-well flat-bottomed cell culture plate are incubated with active fractions in the serum-free medium for 48 hours. (with fractions coming from Q-Sepharose columns 10–15% of volume/well is from the column fraction.) During the last 4 hours of this incubation, 0.5 μCi of tritiated thymidine is added per well. Cells are harvested and the number of counts in cultures containing active material are decreased by 30–90%.

Differentiation is determined by (a) staining of cells on microscope slide with Wright's stain and nonspecific and chloroesterase stains and (b) antibody binding detected by flow cytometry (for HL-60 the following antigens are elevated: major histocompatibility-class II and CD11b).

1. Treves, A. J. et al. (1975) J. Natl. Cancer Inst. 54:777–780.
2. Lee, S. K. et al. (1978) J. Exp. Med. 147:912–922
3. Zarling, J. M. et al. (1979) Nature (London) 280:685–687.
4. Vose, B. M. et al. (1982) Nature (London) 296:359–361.
5. Vose, B. M. et al. (1982) Int. J. Cancer 29:33–39
6. Vanky, F. et al. (1982) J. Exp. Med. 155:83–95
7. Mitsuya, H. et al. (1983) J. Exp. Med. 158:994–999.
8. De Vries, J. E. et al. (1984) J. Immunol. 132:510–519.
9. Slovin, S. F. et al. (1986) J. Immunol. 137:3042–3048
10. Itoh, K. et al. (1986) Cancer Res. 46:3011–3017
11. Rosenberg, S. A. et al. (1986) Science 233:1318–1321
12. Rabinowich, H. et al. (1987) Cancer Res. 47:173–177
13. Miescher, T. et al. (1987) J. Immunol. 138:4004–4011
14. Kradin, R. L. et al. (1987) Cancer Immunol. Immunother. 24:76–85
15. Rosenberg, S. A. et al. (1988) N. Engl. J. Med. 319:1676–1680
16. Smith, K. A. (1988) Science 240:1169–1176
17. Topalian, S. L. et al. (1987) J. Immunol. Methods 102:127–141
18. Packard, B. S. (1987) Proc. Natl. Acad. Sci. USA 84:9015–9019.
19. Kimbauer, R. et al. (1989) J. Immunol. 142:1922–1928

20. Packard, B. S. (1990) In:Progress in Regional Cancer Therapy. eds Jakcez, R. et al. (Springer, Heidelberg), pp. 293–303

21. Smith, K. A. (1988) Adv. Immunol. 42:165–179

All publications mentioned hereinabove are hereby incorporated in their entirety by reference.

While the foregoing invention has been described in some detail for purposes of clarity and understanding, it will be appreciated by one skilled in the art from a reading of this disclosure that various changes in form and detail can be made without departing from the true scope of the invention and appended claims.

What is claimed is:

1. A substantially pure oncoimmunin-lymphoid factor, derived from a human tumor cell line, having a molecular weight of about 45 kD by SDS-PAGE analysis and having the ability to stimulate human T-lymphocyte mitogenesis in an interleukin-2 and interleukin-4 free, serum free medium.

2. The factor according to claim 1, wherein said factor is purified from an interleukin-2 and interleukin-4 free, serum free conditioned medium of the human tumor cell line, wherein said purification comprises the steps of:
   a) subjecting the medium to a Q-Sepharose Fast Flow column;
   b) selecting from the Q-Sepharose column the late eluting fractions displaying bioactivity;
   c) subjecting the late eluting fractions selected in step b) to a Sephacryl S300 column;
   d) selecting the fractions from the Sephacryl column showing bioactivity;
   e) subjecting the fractions selected in step d) to a Mono-Q column;
   f) selecting the fractions from the Mono-Q column showing bioactivity; and
   g) subjecting the fractions selected in step f) to a C$_4$ reverse phase HPLC; wherein said bioactivity is measured as an increase in $^3$H-thymidine incorporation by a tumor infiltrating lymphocyte line.

3. A method of stimulating human T-lymphocyte mitogenesis in a mammal comprising administering to said mammal the factor according to claim 1 in an amount sufficient to stimulate human T-lymphocyte mitogenesis.

4. The method according to claim 3 wherein said mammal is a human.

5. The method according to claim 3 wherein said T-lymphocyte is a tumor infiltrating lymphocyte.

6. A pharmaceutical composition comprising the factor according to claim 1 in an amount effective to stimulate human T-lymphocyte mitogenesis, and a pharmaceutically acceptable diluent, carrier, or excipient.

7. A substantially pure oncoimmunin-myeloid factor, derived from a human tumor cell line, having a molecular weight of about 36 kD by SDS-PAGE analysis and having the ability to inhibit growth or to induce myeloid differentiation in an interleukin-2 and interleukin-4 free, serum free medium.

8. The factor according to claim 7 wherein said factor inhibits growth and induces differentiation of human myeloid leukemic cell line HL-60.

9. A method of inhibiting growth or inducing myeloid differentiation in a mammal comprising administering to said mammal the factor according to claim 7 in an amount sufficient to inhibit growth or induce myeloid differentiation.

10. The method according to claim 9 wherein said mammal is a human.

11. A pharmaceutical composition comprising the factor according to claim 7 in an amount effective to induce myeloid differentiation, and a pharmaceutically acceptable diluent, carrier, or excipient.

12. A method of growing tumor infiltrating lymphocytes ex vivo by culturing them in the presence of the factor according to claim 1.

13. The factor according to claim 2 wherein said bioactivity is determined by the tumor infiltrating lymphocyte line after transfer from an interleukin-2 containing medium to an interleukin-free, serum free medium about 48 hours prior to stimulation.

14. The factor according to claim 7 wherein said factor is purified from an interleukin-2 and interleukin-4 free, serum free conditioned medium of the human tumor cell line, wherein said purification comprises the steps of:
   a) subjecting the medium to a Q-Sepharose Fast Flow column;
   b) selecting from the Q-Sepharose column the early eluting fractions displaying bioactivity;
   c) subjecting the early eluting fractions selected in step b) to a Phenyl Superose column;
   d) selecting the fractions from the Phenyl Superose column showing bioactivity; and
   e) subjecting the fractions selected in step d) to a Sephacryl S-300 column;
   wherein said bioactivity is measured as a decrease in $^3$H-thymidine incorporation by a myeloid cell line and an increase in cell surface expression of CD11b.

15. A method of growing myeloid cells ex vivo by culturing them in the presence of the factor according to claim 7.

* * * * *